US011078240B2

United States Patent
Tottey et al.

(10) Patent No.: US 11,078,240 B2
(45) Date of Patent: Aug. 3, 2021

(54) COVALENTLY FUSED VIRAL COAT PROTEINS FOR THE DISPLAY OF TARGET MOLECULES

(71) Applicant: Fraunhofer USA Inc., Newark, DE (US)

(72) Inventors: Stephen Tottey, Swarthmore, PA (US); Konstantin Musiychuk, Wilmington, DE (US)

(73) Assignee: Fraunhofer USA Inc., Newark, DE (US)

( * ) Notice: Subject to any disclaimer, the term of this patent is extended or adjusted under 35 U.S.C. 154(b) by 72 days.

(21) Appl. No.: 16/346,315

(22) PCT Filed: Nov. 10, 2017

(86) PCT No.: PCT/US2017/061134
§ 371 (c)(1),
(2) Date: Apr. 30, 2019

(87) PCT Pub. No.: WO2018/089814
PCT Pub. Date: May 17, 2018

(65) Prior Publication Data
US 2020/0181203 A1 Jun. 11, 2020

Related U.S. Application Data

(60) Provisional application No. 62/420,993, filed on Nov. 11, 2016.

(51) Int. Cl.
| | | |
|---|---|---|
| *C12N 15/82* | (2006.01) | |
| *C07K 14/415* | (2006.01) | |
| *C12N 9/22* | (2006.01) | |
| *C12N 15/90* | (2006.01) | |
| *A61K 39/00* | (2006.01) | |
| *C07K 14/005* | (2006.01) | |
| *A61K 39/015* | (2006.01) | |
| *A61K 39/12* | (2006.01) | |
| *C12N 15/11* | (2006.01) | |

(52) U.S. Cl.
CPC .......... *C07K 14/005* (2013.01); *A61K 39/015* (2013.01); *A61K 39/12* (2013.01); *C12N 15/111* (2013.01); *A61K 2039/5258* (2013.01); *C07K 2319/00* (2013.01); *C12N 2760/16134* (2013.01)

(58) Field of Classification Search
CPC .......... C12N 15/8261; C12N 15/8271; C12N 15/8247; Y02A 40/146; C07K 14/415
See application file for complete search history.

(56) References Cited

U.S. PATENT DOCUMENTS

| | | | |
|---|---|---|---|
| 7,270,821 B2 | 9/2007 | Gehin et al. | |
| 2012/0219579 A1* | 8/2012 | Yusibov | C07K 14/005 424/192.1 |
| 2016/0122420 A1 | 5/2016 | Rowlands et al. | |
| 2016/0185826 A1* | 6/2016 | Lin | C12N 7/00 424/189.1 |

FOREIGN PATENT DOCUMENTS

WO 0177158 A1 10/2001

OTHER PUBLICATIONS

Jones, R.M., et al., "A Plant-Produced Pfs25 VLP Malaria Vaccine Candidate Induces Persistent Transmission Blocking Antibodies against Plasmodium falciparum in Immunized Mice," Nov. 18, 2013, vol. 8(11), p. e79538 (10 pgs), PLOS ONE.
Yusibov, V., et al., "Antigens Produced in Plants by Infection with Chimeric Plant Viruses Immunize against Rabies Virus and HIV-1," May 1, 1997, vol. 94, pp. 5784-5788, Proceedings of the National Academy of Sciences.
Schwarz, B., et al., "Biomedical and Catalytic Opportunities of Virus-Like Particles in Nanotechnology," Nov. 8, 2016, vol. 97, pp. 1-57, Advances in Virus Research.
Supplementary European Search Report for EP Application No. 17868629, dated May 27, 2020, 10 pages.
International Preliminary Report on Patentability and Written Opinion for International Application No. PCT/US2017/061134, dated May 14, 2019, 7 pages.
International Search Report for PCT Application No. PCT/US2017/061134 dated Feb. 20, 2018 by Lee W. Young.
Peyret et al., PLoS ONE, 10(4):e0120751, 20 pages (2015).

\* cited by examiner

*Primary Examiner* — Barry A Chestnut
(74) *Attorney, Agent, or Firm* — RatnerPrestia

(57) ABSTRACT

A fusion protein comprising a first recombinant viral coat protein, a second recombinant viral coat protein and a first linkage peptide is provided. The first recombinant viral coat protein is linked to N-terminus of the first linkage peptide. The second recombinant viral coat protein is linked to C-terminus of the first linkage peptide. The first and second recombinant viral coat proteins are derived from the coat protein (CP) of alfalfa mosaic virus (AIMV). The fusion protein may form a virus like particle (VLP). Where the fusion protein further comprises a target protein, the target protein may be displayed on the surface of the VLP. Also provided are methods for producing the fusion protein and the VLP as well as the uses of the fusion protein and/or the VLP.

16 Claims, 20 Drawing Sheets
Specification includes a Sequence Listing.

Fig. 1

MSSSQKKAGGKAGGKPTKRSQNYAALRKAQLPKPPALKVPVVKPTNTILPQTGCVWQSLGTPLSLSSFNGLGVRFLYSFLKDFAGPRILEEDLIYRMV
FSITPSYAGTFCLTDDVTTEDGRAVAHGNPMQEFPHGAFHANEKFGFELVFTAPTHAGMQNQNFKHSYAVALCLDFDAQPEGSKNPSYRFNEVWV
ERKAFPRAGPLRSLITVGLFDEADDLDRH (SEQ ID NO: 1)

GGGGSGGGGSGGGGS (SEQ ID NO: 2)

SSSQKKAGGKAGGKPTGGGGSGGGGSGGGGSPVVKPTNTILPQTGCVWQSLGTPLSLSSFNGLGVRFLYSFLKDFAGPRILEEDLIYRMVFSITPSY
AGTFCLTDDVTTEDGRAVAHGNPMQEFPHGAFHANEKFGFELVFTAPTHAGMQNQNFKHSYAVALCLDFDAQPEGSKNPSYRFNEVWVERKAFP
RAGPLRSLITVGLFDEADDLDRH (SEQ ID NO: 3)

SSSQKKAGGKAGGKPTPVVKPTNTILPQTGCVWQSLGTPLSLSSFNGLGVRFLYSFLKDFAGPRILEEDLIYRMVFSITPSYAGTFCLTDDVTTEDGR
AVAHGNPMQEFPHGAFHANEKFGFELVFTAPTHAGMQNQNFKHSYAVALCLDFDAQPEGSKNPSYRFNEVWVERKAFPRAGPLRSLITVGLFDEA
DDLDRH (SEQ ID NO: 4)

SSSQKKAGGKAGGKPTGGGGSGGGGSGGGGSPVVKPTNTILPQTGCVWQSLGTPLSLSSFNGLGVRFLYSFLKDFAGPRILEEDLIYRMVFSITPSY
AGTFCLTDDVTTEDGRAVAHGNPMQEFPHGAFHANEKFGFELVFTAPTHAGMQNQNFKHSYAVALCLDFDAQPEGSKNPSYRFNEVWVERKAFP
RAGPLRSLITVGLFDEADDLDRHGGGGSGGGGSGGGGSSSQKKAGGKAGGKPTPVVKPTNTILPQTGCVWQSLGTPLSLSSFNGLGVRFLYSFLK
DFAGPRILEEDLIYRMVFSITPSYAGTFCLTDDVTTEDGRAVAHGNPMQEFPHGAFHANEKFGFELVFTAPTHAGMQNQNFKHSYAVALCLDFDAQ
PEGSKNPSYRFNEVWVERKAFPRAGPLRSLITVGLFDEADDLDRHHHHHH (SEQ ID NO: 5)

Fig. 7
A.
B. Negative stained TEM of CMB-02412 final product
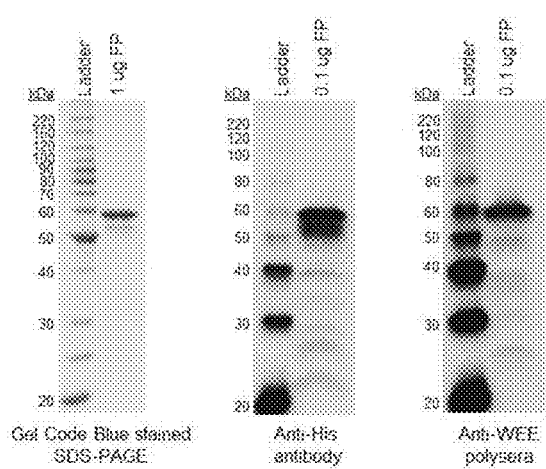
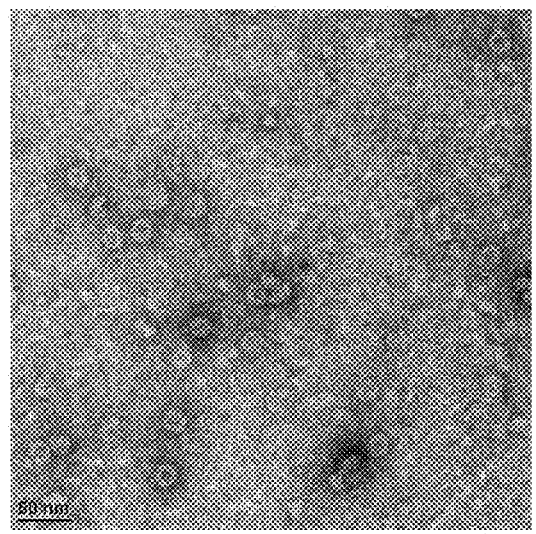

Fig. 8
A.
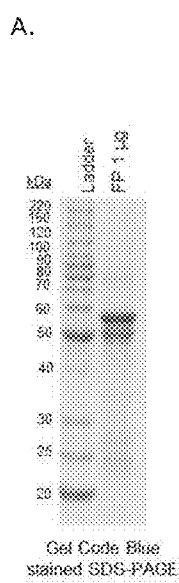 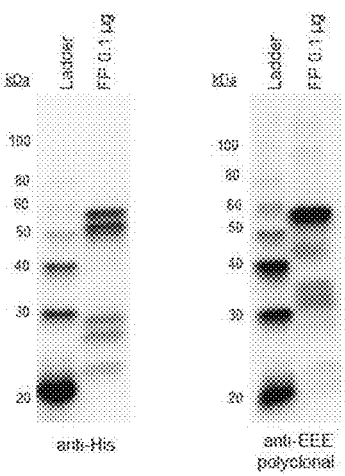
B. Negative stained TEM of CMB-02383 final product
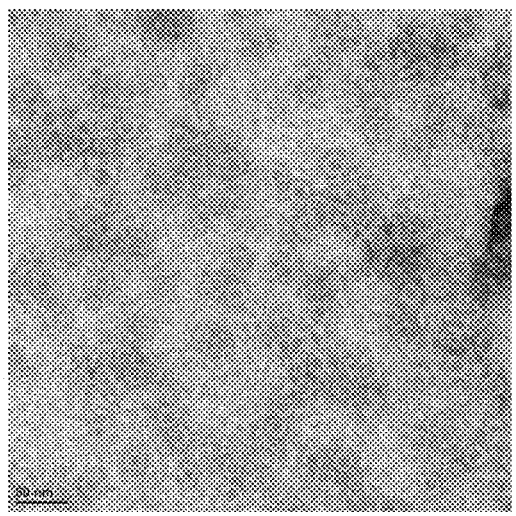

2$^{nd}$ Generation Designs

| Name | Description | Ratio (fusion:total) | CP-VLP recovery (mg/kg) | Particle formation |
|---|---|---|---|---|
| A85 | Original molecule | Variable (1 : 4-7) | ~4mg/kg | Yes |
| B29 | 3 Point mutations at A85 cleavage sites | 1 : 2 | ~ 30mg/kg | Yes |
| B30 | 22 amino acids at cleavage region removed | 1 : 1 | ~ 200mg/kg | No |
| B64 | 22 amino acids at cleavage region replaced | 1 : 1 | ~ 200mg/kg | No |

Fig. 14
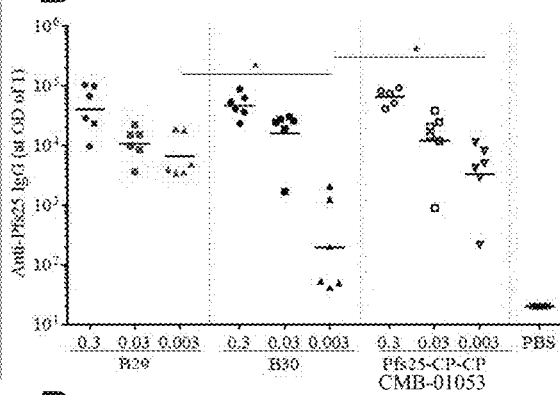
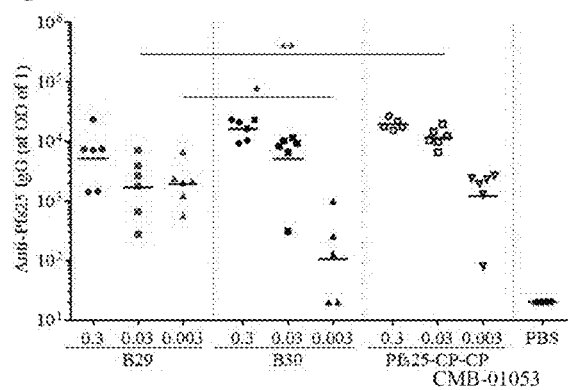

Fig. 15

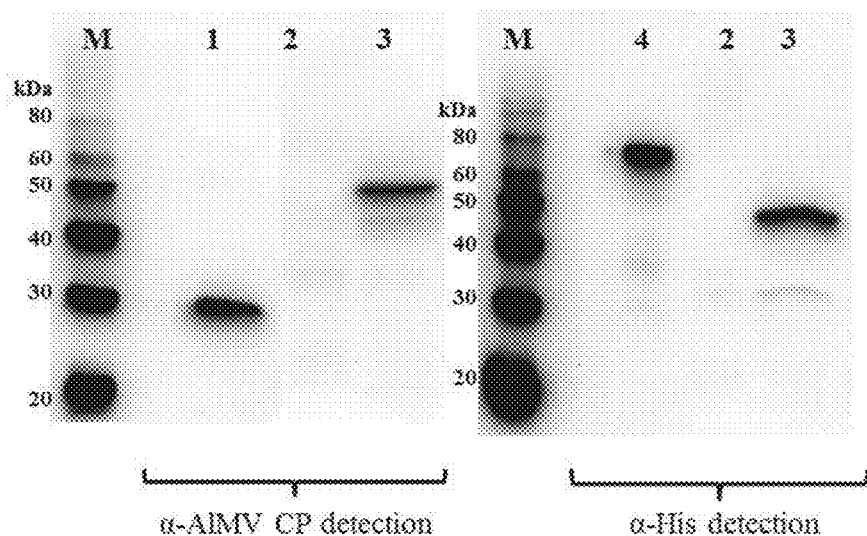

SEQUENCE LISTING

```
<160> NUMBER OF SEQ ID NOS: 5

<210> SEQ ID NO 1
<211> LENGTH: 221
<212> TYPE: PRT
<213> ORGANISM: Alfalfa mosaic virus
```

<400> SEQUENCE: 1

Met Ser Ser Ser Gln Lys Lys Ala Gly Gly Lys Ala Gly Lys Pro Thr
1               5                   10                  15

Lys Arg Ser Gln Asn Tyr Ala Ala Leu Arg Lys Ala Gln Leu Pro Lys
            20                  25                  30

Pro Pro Ala Leu Lys Val Pro Val Lys Pro Thr Asn Thr Ile Leu
        35                  40                  45

Pro Gln Thr Gly Cys Val Trp Gln Ser Leu Gly Thr Pro Leu Ser Leu
    50                  55                  60

Ser Ser Phe Asn Gly Leu Gly Val Arg Phe Leu Tyr Ser Phe Leu Lys
65                  70                  75                  80

Asp Phe Ala Gly Pro Arg Ile Leu Glu Glu Asp Leu Ile Tyr Arg Met
                85                  90                  95

Val Phe Ser Ile Thr Pro Ser Tyr Ala Gly Thr Phe Cys Leu Thr Asp
            100                 105                 110

Asp Val Thr Thr Glu Asp Gly Arg Ala Val Ala His Gly Asn Pro Met
        115                 120                 125

Gln Glu Phe Pro His Gly Ala Phe His Ala Asn Glu Lys Phe Gly Phe
    130                 135                 140

Glu Leu Val Phe Thr Ala Pro Thr His Ala Gly Met Gln Asn Gln Asn
145                 150                 155                 160

Phe Lys His Ser Tyr Ala Val Ala Leu Cys Leu Asp Phe Asp Ala Gln
                165                 170                 175

Pro Glu Gly Ser Lys Asn Pro Ser Tyr Arg Phe Asn Glu Val Trp Val
            180                 185                 190

Glu Arg Lys Ala Phe Pro Arg Ala Gly Pro Leu Arg Ser Leu Ile Thr
        195                 200                 205

Val Gly Leu Phe Asp Glu Ala Asp Asp Leu Asp Arg His
    210                 215                 220

<210> SEQ ID NO 2
<211> LENGTH: 15
<212> TYPE: PRT
<213> ORGANISM: Artificial Sequence
<220> FEATURE:
<223> OTHER INFORMATION: Synthetic

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 213
<212> TYPE: PRT
<213> ORGANISM: Artificial Sequence
<220> FEATURE:
<223> OTHER INFORMATION: Synthetic

<400> SEQUENCE: 3

Ser Ser Ser Gln Lys Lys Ala Gly Gly Lys Ala Gly Lys Pro Thr Gly
1               5                   10                  15

Gly Gly Gly Ser Gly Gly Gly Gly Ser Gly Gly Gly Gly Ser Pro Val
            20                  25                  30

Val Lys Pro Thr Asn Thr Ile Leu Pro Gln Thr Gly Cys Val Trp Gln
        35                  40                  45

Ser Leu Gly Thr Pro Leu Ser Leu Ser Ser Phe Asn Gly Leu Gly Val
    50                  55                  60

```
Arg Phe Leu Tyr Ser Phe Leu Lys Asp Phe Ala Gly Pro Arg Ile Leu
 65                  70                  75                  80

Glu Glu Asp Leu Ile Tyr Arg Met Val Phe Ser Ile Thr Pro Ser Tyr
                 85                  90                  95

Ala Gly Thr Phe Cys Leu Thr Asp Asp Val Thr Thr Glu Asp Gly Arg
            100                 105                 110

Ala Val Ala His Gly Asn Pro Met Gln Glu Phe Pro His Gly Ala Phe
        115                 120                 125

His Ala Asn Glu Lys Phe Gly Phe Glu Leu Val Phe Thr Ala Pro Thr
130                 135                 140

His Ala Gly Met Gln Asn Gln Asn Phe Lys His Ser Tyr Ala Val Ala
145                 150                 155                 160

Leu Cys Leu Asp Phe Asp Ala Gln Pro Glu Gly Ser Lys Asn Pro Ser
                165                 170                 175

Tyr Arg Phe Asn Glu Val Trp Val Glu Arg Lys Ala Phe Pro Arg Ala
                180                 185                 190

Gly Pro Leu Arg Ser Leu Ile Thr Val Gly Leu Phe Asp Glu Ala Asp
            195                 200                 205

Asp Leu Asp Arg His
            210

<210> SEQ ID NO 4
<211> LENGTH: 198
<212> TYPE: PRT
<213> ORGANISM: Artificial Sequence
<220> FEATURE:
<223> OTHER INFORMATION: Synthetic

<400> SEQUENCE: 4

Ser Ser Ser Gln Lys Lys Ala Gly Gly Lys Ala Gly Lys Pro Thr Pro
 1               5                   10                  15

Val Val Lys Pro Thr Asn Thr Ile Leu Pro Gln Thr Gly Cys Val Trp
                20                  25                  30

Gln Ser Leu Gly Thr Pro Leu Ser Leu Ser Ser Phe Asn Gly Leu Gly
            35                  40                  45

Val Arg Phe Leu Tyr Ser Phe Leu Lys Asp Phe Ala Gly Pro Arg Ile
        50                  55                  60

Leu Glu Glu Asp Leu Ile Tyr Arg Met Val Phe Ser Ile Thr Pro Ser
 65                  70                  75                  80

Tyr Ala Gly Thr Phe Cys Leu Thr Asp Asp Val Thr Thr Glu Asp Gly
                 85                  90                  95

Arg Ala Val Ala His Gly Asn Pro Met Gln Glu Phe Pro His Gly Ala
            100                 105                 110

Phe His Ala Asn Glu Lys Phe Gly Phe Glu Leu Val Phe Thr Ala Pro
        115                 120                 125

Thr His Ala Gly Met Gln Asn Gln Asn Phe Lys His Ser Tyr Ala Val
130                 135                 140

Ala Leu Cys Leu Asp Phe Asp Ala Gln Pro Glu Gly Ser Lys Asn Pro
145                 150                 155                 160

Ser Tyr Arg Phe Asn Glu Val Trp Val Glu Arg Lys Ala Phe Pro Arg
                165                 170                 175

Ala Gly Pro Leu Arg Ser Leu Ile Thr Val Gly Leu Phe Asp Glu Ala
            180                 185                 190

Asp Asp Leu Asp Arg His
            195
```

<210> SEQ ID NO 5
<211> LENGTH: 431
<212> TYPE: PRT
<213> ORGANISM: Artificial Sequence
<220> FEATURE:
<223> OTHER INFORMATION: Synthetic

<400> SEQUENCE: 5

```
Ser Ser Ser Gln Lys Lys Ala Gly Gly Lys Ala Gly Lys Pro Thr Gly
1               5                   10                  15

Gly Gly Gly Ser Gly Gly Gly Ser Gly Gly Gly Ser Pro Val
            20                  25                  30

Val Lys Pro Thr Asn Thr Ile Leu Pro Gln Thr Gly Cys Val Trp Gln
            35                  40                  45

Ser Leu Gly Thr Pro Leu Ser Leu Ser Ser Phe Asn Gly Leu Gly Val
        50                  55                  60

Arg Phe Leu Tyr Ser Phe Leu Lys Asp Phe Ala Gly Pro Arg Ile Leu
65                  70                  75                  80

Glu Glu Asp Leu Ile Tyr Arg Met Val Phe Ser Ile Thr Pro Ser Tyr
                85                  90                  95

Ala Gly Thr Phe Cys Leu Thr Asp Asp Val Thr Thr Glu Asp Gly Arg
            100                 105                 110

Ala Val Ala His Gly Asn Pro Met Gln Glu Phe Pro His Gly Ala Phe
        115                 120                 125

His Ala Asn Glu Lys Phe Gly Phe Glu Leu Val Phe Thr Ala Pro Thr
    130                 135                 140

His Ala Gly Met Gln Asn Gln Asn Phe Lys His Ser Tyr Ala Val Ala
145                 150                 155                 160

Leu Cys Leu Asp Phe Asp Ala Gln Pro Glu Gly Ser Lys Asn Pro Ser
                165                 170                 175

Tyr Arg Phe Asn Glu Val Trp Val Arg Lys Ala Phe Pro Arg Ala
            180                 185                 190

Gly Pro Leu Arg Ser Leu Ile Thr Val Gly Leu Phe Asp Glu Ala Asp
        195                 200                 205

Asp Leu Asp Arg His Gly Gly Gly Ser Gly Gly Gly Ser Gly
    210                 215                 220

Gly Gly Ser Ser Ser Ser Gln Lys Lys Ala Gly Gly Lys Ala Gly
225                 230                 235                 240

Lys Pro Thr Pro Val Val Lys Pro Thr Asn Thr Ile Leu Pro Gln Thr
                245                 250                 255

Gly Cys Val Trp Gln Ser Leu Gly Thr Pro Leu Ser Leu Ser Ser Phe
            260                 265                 270

Asn Gly Leu Gly Val Arg Phe Leu Tyr Ser Phe Leu Lys Asp Phe Ala
        275                 280                 285

Gly Pro Arg Ile Leu Glu Glu Asp Leu Ile Tyr Arg Met Val Phe Ser
    290                 295                 300

Ile Thr Pro Ser Tyr Ala Gly Thr Phe Cys Leu Thr Asp Asp Val Thr
305                 310                 315                 320

Thr Glu Asp Gly Arg Ala Val Ala His Gly Asn Pro Met Gln Glu Phe
                325                 330                 335

Pro His Gly Ala Phe His Ala Asn Glu Lys Phe Gly Phe Glu Leu Val
            340                 345                 350

Phe Thr Ala Pro Thr His Ala Gly Met Gln Asn Gln Asn Phe Lys His
        355                 360                 365
```

-continued

```
Ser Tyr Ala Val Ala Leu Cys Leu Asp Phe Asp Ala Gln Pro Glu Gly
    370             375             380

Ser Lys Asn Pro Ser Tyr Arg Phe Asn Glu Val Trp Val Glu Arg Lys
385             390             395             400

Ala Phe Pro Arg Ala Gly Pro Leu Arg Ser Leu Ile Thr Val Gly Leu
                405             410             415

Phe Asp Glu Ala Asp Asp Leu Asp Arg His His His His His His
                420             425             430
```

COVALENTLY FUSED VIRAL COAT PROTEINS FOR THE DISPLAY OF TARGET MOLECULES

CROSS-REFERENCE TO RELATED APPLICATION

This application is a U.S. national phase of International Application No. PCT/US2017/061134, filed Nov. 10, 2017, claiming priority to U.S. Provisional Application No. 62/420,993, filed Nov. 11, 2016, the entire disclosure of each of which is incorporated herein by reference in its entirety for all purposes.

FIELD OF THE INVENTION

The invention relates to covalently fused viral coat proteins and virus like particles formed thereby to display target molecules.

BACKGROUND OF THE INVENTION

Virus-like particle (VLP) vaccines are recombinantly produced vaccines that display desirable antigens on repetitive, high-density displays, and have been shown to increase the immune response to the antigens. All commercially available recombinantly produced vaccines are in the form of VLPs.

Peyret et al. have reported that the major insertion region (MIR) on hepatitis B core protein HBcAg allows insertion of a foreign sequence for displaying a foreign protein (e.g., a single-domain antibody fragment) encoded by the foreign sequence on the tips of surface spike structures on the outside VLPs assembled by a single polypeptide chain by tandem fusion of two HBcAg open reading frames, and that this tandem core strategy allows insertion of a large heterologous sequence in one of the two MIRs in each spike without compromising VLP formation. (Peyret et al. (2015) PLoS ONE 10(4):e0120751.doi:10.1371/journal.pone.0120751; U.S. Patent Application Publication No. 2016/0122420 A1). As the MIR site is the most exposed and the majority of the antibodies induced by HBc particles recognize this region, the immunodominance of this antigenic site is transferred to the foreign sequence inserted at the MIR site. (Peyret et al. (2015) PLoS ONE 10(4): e0120751.doi:10.1371/journal.pone.0120751).

Most viral coat proteins do not have the antigenic MIR site of the HBcAg protein for making VLP vaccines. Thus, there remains a need for fusion proteins of viral coat proteins such as alfalfa mosaic virus (AIMV) coat protein (CP) useful for making effective VLP vaccines.

SUMMARY OF THE INVENTION

The present invention relates to fusion proteins comprising two or more recombinant viral coat proteins and an optional target protein, and virus like particles (VLPs) formed by the fusion proteins.

The present invention provides a fusion protein comprising a first recombinant viral coat protein, a second recombinant viral coat protein and a first linkage peptide. The first recombinant viral coat protein is linked to N-terminus of the first linkage peptide and the second recombinant viral coat protein is linked to C-terminus of the first linkage peptide. The first recombinant viral coat protein comprises an amino acid sequence at least 80% identical to the amino acid sequence of the coat protein (CP) of alfalfa mosaic virus (AIMV) (SEQ ID NO: 1). The second recombinant viral coat protein comprises an amino acid sequence at least 80% identical to SEQ ID NO: 1. The first linkage peptide may consist of SEQ NO: 2.

The present invention also provides a fusion protein comprising a target protein, a first recombinant viral coat protein, a second recombinant viral coat protein and a first linkage peptide. The target protein is at N-terminus of the first recombinant viral coat protein. The first recombinant viral coat protein is linked to N-terminus of the first linkage peptide. The second recombinant viral coat protein is linked to C-terminus of the first linkage peptide. The first recombinant viral coat protein comprises an amino acid sequence at least 80% identical to the coat protein (CP) of alfalfa mosaic virus (AIMV) (SEQ ID NO: 1). The second recombinant viral coat protein comprises an amino acid sequence at least 80% identical to SEQ ID NO: 1. The first linkage peptide may consist of SEQ ID NO: 2.

Where the fusion protein comprises the target protein, the fusion protein may further comprise a second linkage peptide, wherein the target protein is linked to N-terminus of the second linkage peptide and the first recombinant viral coat protein is linked to C-terminus of the second linkage peptide. The second linkage peptide may consist of SEQ ID NO: 2.

The first recombinant viral coat protein may comprise an amino acid sequence at least 80% identical to SEQ ID NO: 1 with a mutation of one or more trypsin sites. The first recombinant viral coat protein may comprise an amino acid sequence at least 80% identical to SEQ ID NO: 1 with a mutation of a chymotrypsin site. The first recombinant viral coat protein may comprise an amino acid sequence at least 80% identical to SEQ ID NO: 1 with a mutation of one or more in planta digestion sites.

The first recombinant viral coat protein may comprise an amino acid sequence at least 80% identical to SEQ ID NO: 1 with a deletion, insertion or substitution at residues 17-38 of SEQ ID NO: 1. Residues 17-38 of SEQ ID NO: 1 may be substituted with a third linkage peptide consisting of SEQ ID NO: 2. The first recombinant viral coat protein may consist of SEQ ID NO: 3. The first recombinant viral coat protein may further comprise a mutation of one or more trypsin sites.

The second recombinant viral coat protein may comprise an amino acid sequence at least 80% identical to SEQ ID NO: 1 with a mutation of one or more trypsin sites. The second recombinant viral coat protein may comprise an amino acid sequence at least 80% identical to SEQ ID NO: 1 with a mutation of a chymotrypsin site. The second recombinant viral coat protein comprises an amino acid sequence at least 80% identical to SEQ ID NO: 1 with a mutation of one or more in planta digestion sites.

The second recombinant viral coat protein may comprise an amino acid sequence at least 80% identical to SEQ ID NO: 1 with a deletion, insertion or substitution at residues 17-38 of SEQ ID NO: 1. The second recombinant viral coat protein may consist of SEQ ID NO: 4. Residues 17-38 of SEQ ID NO: 1 may be substituted with a fourth linkage peptide. The fourth linkage peptide may consist of SEQ ID NO: 2. The second recombinant viral coat protein may further comprise a mutation of one or more trypsin sites.

The fusion protein of the present invention may comprise SEQ ID NO: 5.

Where the fusion protein comprises a target protein, the target protein may be an agent selected from the group consisting of an immunogenic agent, a therapeutic agent, a diagnostic agent and an enzyme. The target protein may be an immunogenic agent. The target protein may be a therapeutic agent. The target protein may be a diagnostic agent. The target protein may be an enzyme.

For each fusion protein of the present invention, a method for producing the fusion protein is provided. The method comprises introducing into cells a nucleic acid molecule encoding the fusion protein, and expressing the fusion protein in the cells. Thereby, the fusion protein is produced.

Where the fusion protein comprises a target protein, a method for producing the fusion protein is provided. The method comprises introducing into cells a nucleic acid molecule encoding the fusion protein, and expressing the fusion protein in the cells. Thereby, the fusion protein is produced. The target protein may be an agent selected from the group consisting of an immunogenic agent, a therapeutic agent, a diagnostic agent and an enzyme. The target protein may be an immunogenic agent. The target protein may be a therapeutic agent. The target protein may be a diagnostic agent. The target protein may be an enzyme.

The fusion protein production method may further comprise purifying the fusion protein from the cells. The cells may be in a plant or a portion thereof. The cells may be yeast cells. The cells may be insect cells. The cells may be mammalian cells.

For each fusion protein of the present invention, a composition comprising the fusion protein is provided. The composition may further comprise a pharmaceutically acceptable excipient.

A virus like particle (VLP) formed by the fusion protein of the present invention is provided. Where the fusion protein comprises a target protein, the target protein is displayed on the surface the virus like particle.

The VLP may be formed in a cell, an organism or a portion of an organism. The cell may be selected from the group consisting of a plant cell, a yeast cell, an insect cell and a mammalian cell. The cell may be in a plant or a portion thereof. The plant may be a *Nicotiana* species. The cell may be a yeast cell. The cell may be an insect cell. The cell may be a mammalian cell.

For the VLPs of the present invention, a composition comprising the VLPs is provided. At least 50% of the virus like particles may have a diameter within less than 50% of an average diameter of the virus like particles. The composition may further comprise a pharmaceutically acceptable excipient.

For a fusion protein according to the present invention, a method of producing virus like particles (VLPs) by the fusion protein is provided. The method comprises introducing into a cell, an organism or a portion of the organism a nucleic acid molecule encoding the fusion protein, expressing the fusion protein in the cell, the organism or the portion of the organism, and forming VLPs by the fusion protein. Thereby, the virus like particles are produced.

For a fusion protein comprising a target protein according to the present invention, a method of producing virus like particles (VLPs) by the fusion protein is provided. The method comprises introducing into a cell, an organism or a portion of the organism a nucleic acid molecule encoding the fusion protein, expressing the fusion protein in the cell, the organism or the portion of the organism, and forming VLPs by the fusion protein. Thereby, the VLPs are produced and the target protein is displayed on the surface of the VLPs.

In one embodiment, the VLPs are formed in the cell, the organism or the portion of the organism. The VLP production method may further comprise purifying the VLPs from the cell, the organism or the portion of the organism.

In another embodiment, the VLP production method further comprises purifying the fusion protein from the cell, the organism or the portion of the organism before VLP formation.

According to the VLP production method of the present invention, at least 50% of the virus like particles may have a diameter within less than 50% of an average diameter of the virus like particles. The VLPs may be formed by at least 50% of the fusion protein.

A method of inducing an immunological response in a subject is provided. The method comprises administering to the subject an effective amount of a fusion protein comprising an immunogenic agent as a target protein according to the present invention or VLPs formed by the fusion protein.

A method of treating a disease or condition in a subject is provided. The method comprises administering to the subject an effective amount of a fusion protein comprising a therapeutic agent as a target protein according to the present invention or VLPs formed by the fusion protein.

A method of detecting a biomarker in a sample from a subject is provided. The method comprises contacting the sample with an effective amount of a fusion protein comprising a diagnostic agent as a target protein according to the present invention or VLPs formed by the fusion protein. The diagnostic agent binds the biomarker.

A method of catalyzing a reaction by a reagent is provided. The method comprises contacting the reagent with an effective amount of a fusion protein comprising an enzyme as a target protein according to the present invention or VLPs formed by the fusion protein. The enzyme catalyzes the reaction.

BRIEF DESCRIPTION OF THE FIGURES

FIG. 1 shows the amino acid sequences for the coat protein (CP) of alfalfa mosaic virus (AIMV) (SEQ ID NO: 1), a linkage peptide (SEQ ID NO: 2), a first recombinant viral coat protein (SEQ ID NO: 3), a second recombinant viral protein (SEQ ID NO: 4) and a fusion protein (SEQ ID NO: 5).

CMB-02039, CMB-02079, CMB-02011, CMB-02059, CMB-02011, and CMB-02059 displaying the influenza antigens on VLPs.

FIG. 7 shows characterization of the Western Equine encephalitis virus domain as a $CP^2$ fusion protein. A) Gel code Blue stained SDS-PAGE of Western Equine encephalitis virus domain $CP^2$ fusion protein CMB-02412, and recognition by anti-His antibody, and anti-Western Equine encephalitis (WEE) virus antibody. (B) Negatively stained transmission electron microscopy image of CMB-02412 displaying the Western Equine encephalitis virus domain as a VLP.

FIG. 8 shows characterization of the Eastern Equine encephalitis virus domain as a $CP^2$ fusion protein. (A) Gel code Blue stained SDS-PAGE of Eastern Equine encephalitis virus domain $CP^2$ fusion protein CMB-02383, and recognition by anti-His antibody, and anti-Eastern Equine encephalitis (EEE) virus antibody. (B) Negatively stained transmission electron microscopy image of CMB-02383 displaying the Eastern Equine encephalitis virus domain as VLPs.

Figure 9:
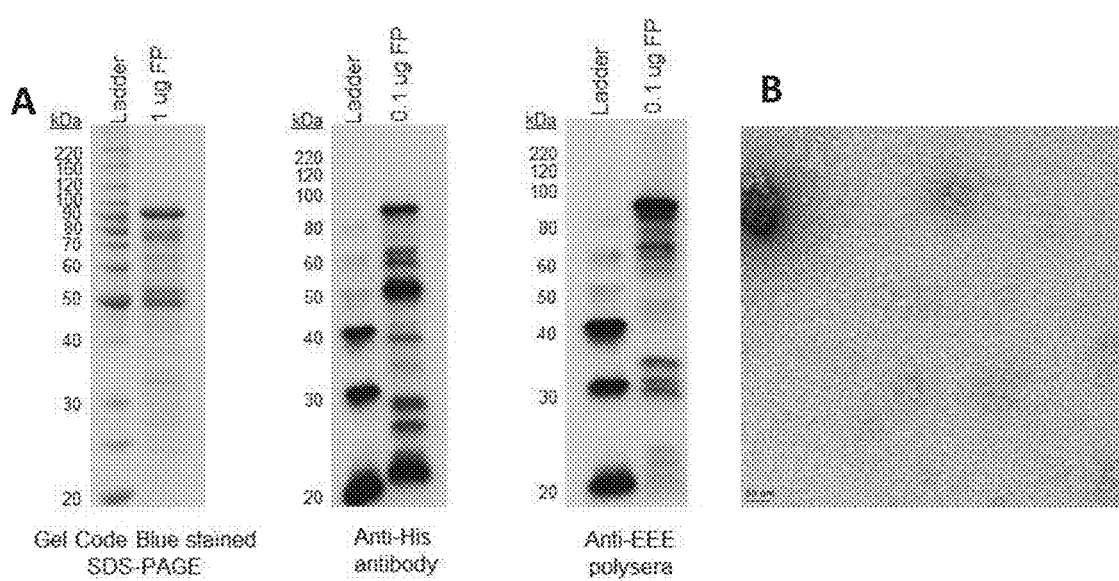

FIG. 9 shows characterization of the Eastern Equine encephalitis virus protein as a $CP^2$ fusion protein. (A) Gel code Blue stained SDS-PAGE of Eastern Equine encephalitis virus $CP^2$ fusion protein CMB-02380, and recognition by anti-His antibody, and anti-Eastern Equine encephalitis virus antibody. (B) Negatively stained transmission electron microscopy image of CMB-02380 displaying the Eastern Equine encephalitis virus protein as VLPs.

Figure 10:
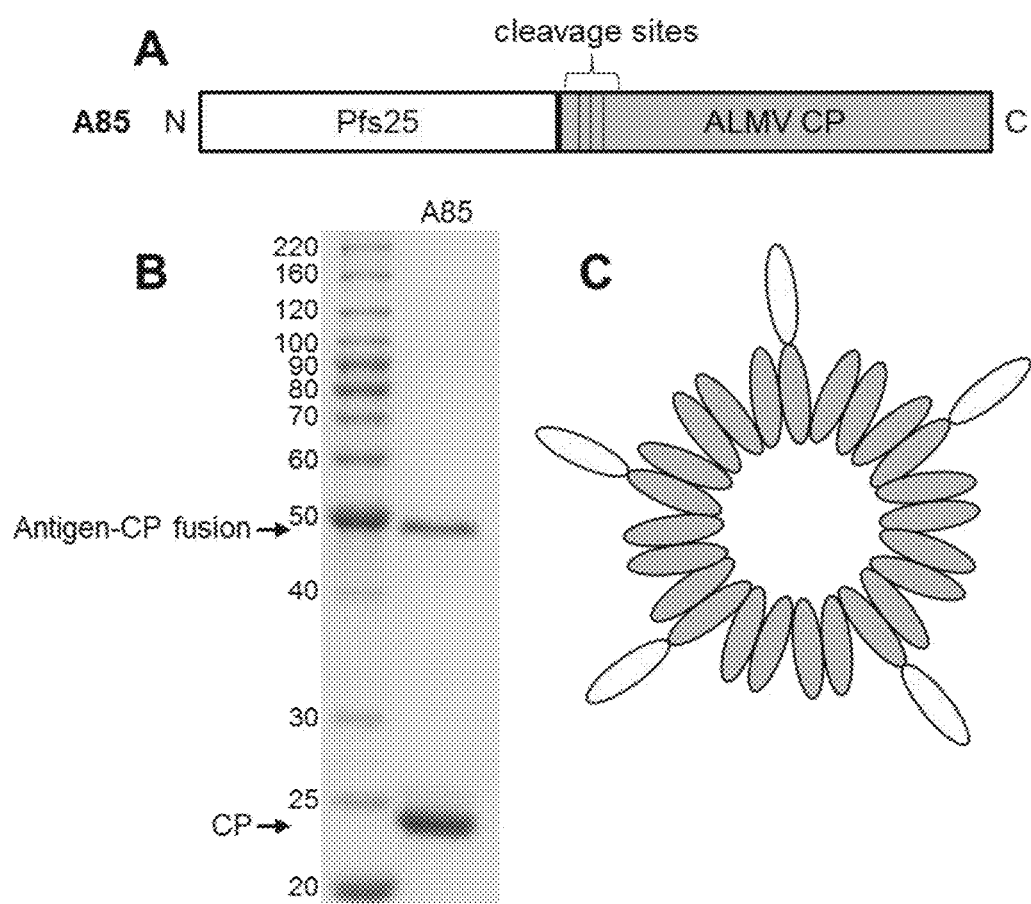

FIG. 10 shows a first generation VLP design. (A) Schematic showing the design of the first generation A85 molecule. (B) SDS-PAGE gel of the purified A85 VLP. (C) Cartoon image of the A85 VLP showing the levels of antigen display.

Figure 11:
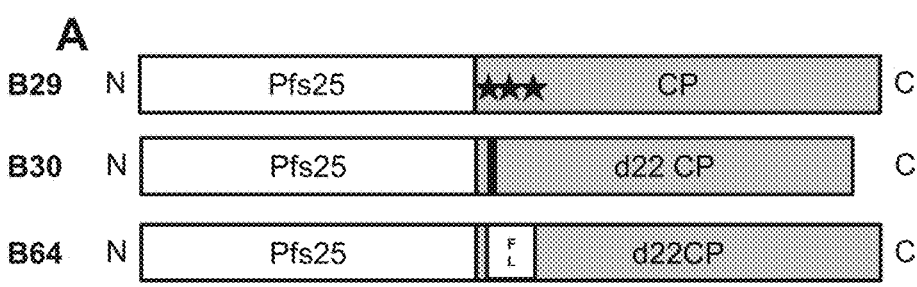

FIG. 11 shows second generation VLP designs. (A) Schematic showing the designs of the second-generation molecules. (B) Table summarizing the results of the second-generation molecules.

Figure 12:
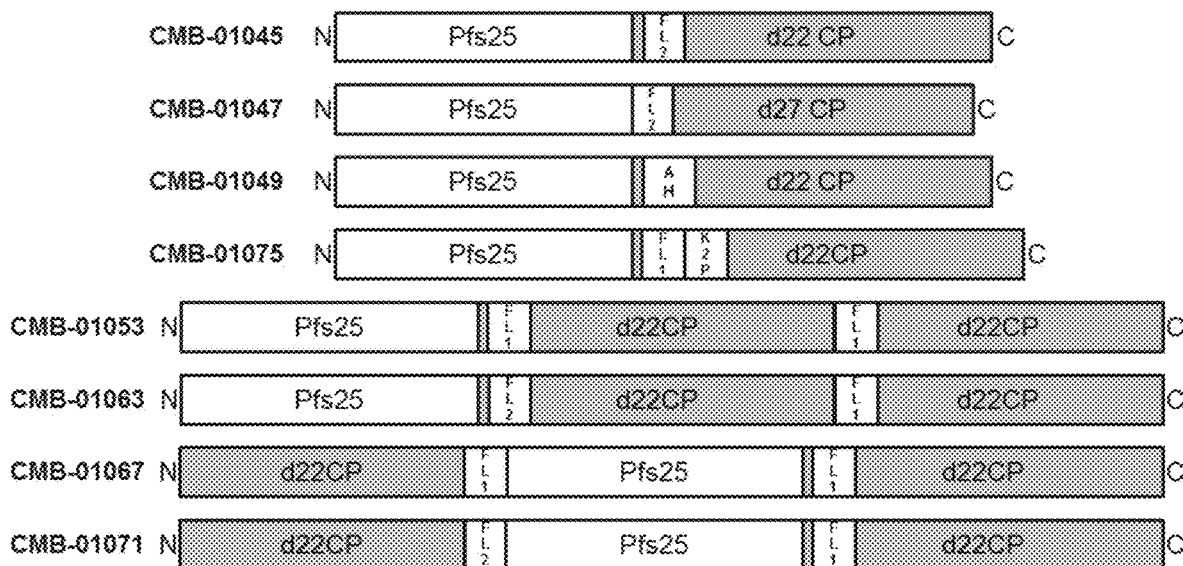

FIG. 12 shows third generation VLP designs. (A) Schematic showing the designs of the third-generation molecules. (B) Table summarizing the results of the third-generation molecules. (ND=not determined).

Figure 13:
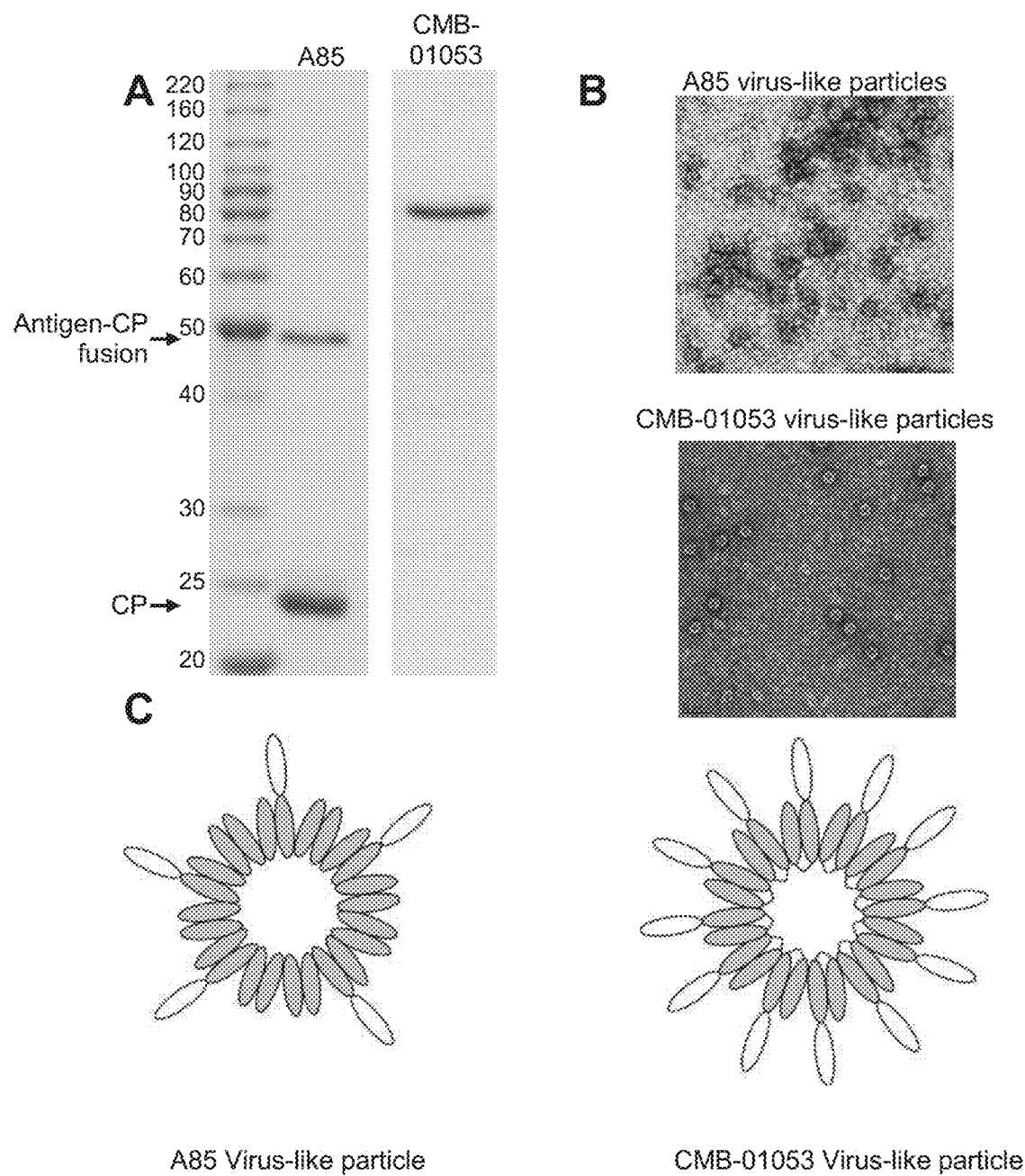

FIG. 13 shows comparison of the A85 VLP to the CMB-01053 VLP. (A) SDS-PAGE gel of the purified A85 and CMB-01053 VLPs. (B) Negatively stained transmission electron microscopy image of purified A85 and CMB-01053 VLPs. (C) Cartoon image of the A85 and CMB-1053 VLPs showing the levels of antigen display.

FIG. 14 shows immunological comparison of VLPs formed by Pfs25-CP fusion proteins B29, B30 and CMB-01053. (A) Animal study design comparing Pfs25-CP fusion proteins. (B) Anti-Pfs25 IgG responses at day 56. (C) Anti-Pfs25 IgG responses at day 168. (D) Standard membrane feeding assay (SMFA) of samples obtained on days 56 (D.56) and 168 (D.168).

Figure 15:
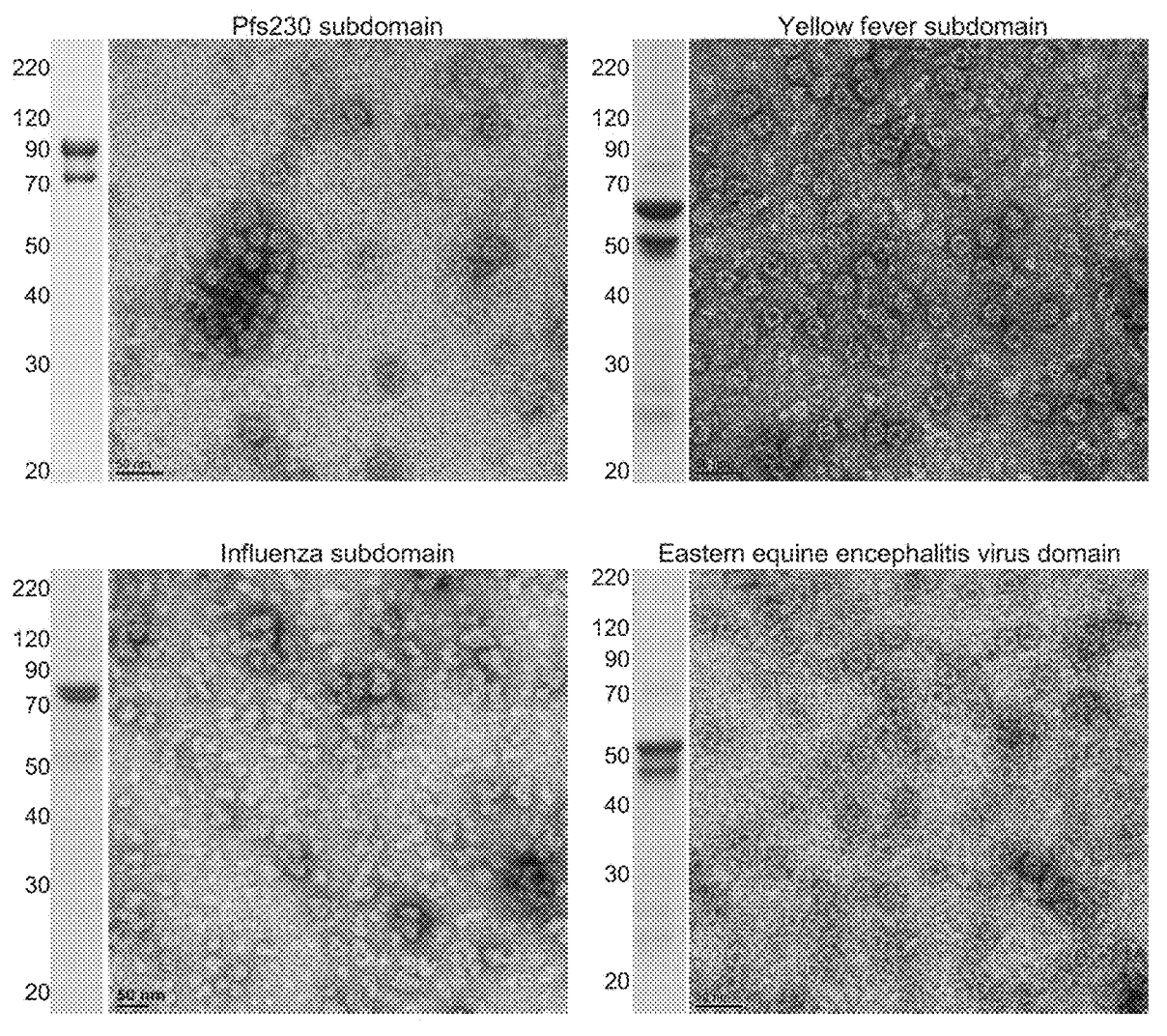

FIG. 15 shows gel code blue stained PAGE and negatively stained transmission electron microscopy image of CP-CP VLPs displaying a variety of antigens: Pfs230 subdomain (top left panel), Yellow fever subdomain (top right panel), influenza subdomain (bottom left panel) and Eastern equine encephalitis virus domain (bottom right panel).

FIG. 16 shows degradation sites in the N-terminus of AIMV CP. (A) In silico identification of trypsin and chymotrypsin sensitive sites of amino acids 2 to 50 of wild-type AIMV CP (SEQ ID NO: 1). (B) Amino acids 2 to 50 of wild-type AIMV CP (SEQ ID NO: 1) with identified sites of in planta digestion indicated by arrows. (C) In silico identification of trypsin and chymotrypsin sensitive sites in the corresponding region from the modified AIMV CP (corresponding to residues 1-42 of SEQ ID NO: 3), showing removal of most of the protease sensitive sites.

FIG. 17 shows expression of fusion protein of SEQ ID NO: 5 in extract of Sf21 insect cells on Western blots, where M—Molecular weight marker; 1—AIMV CP standard; 2—non-transfected insect SF21 cells; 3—transfected insect SF21 cells extract, expressing CP-CP fusion; 4—HAI standard, containing 6×His tag.

Figure 18:
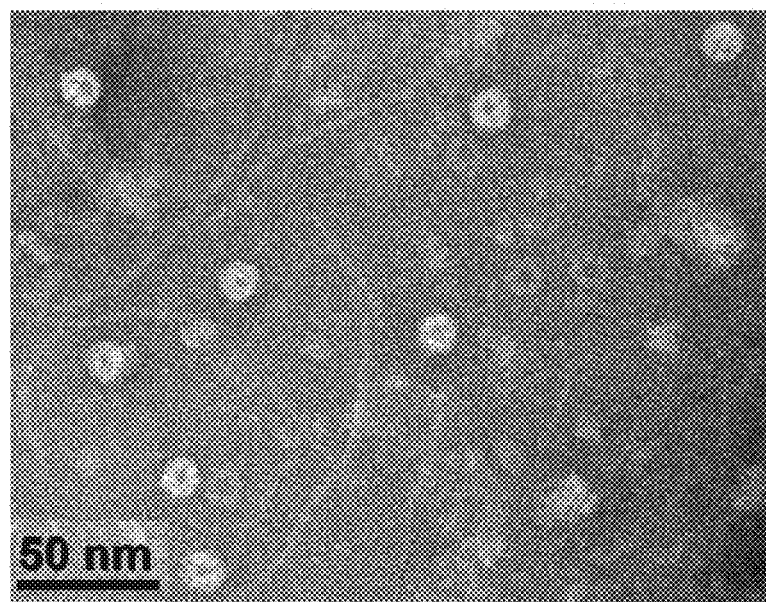

FIG. 18 shows VLPs collected by high-speed centrifugation analyzed by negatively stained transmission electron microscopy (TEM), confirming that fusion protein of SEQ ID NO: 5 expressed in insect cells can form VLPs.

Figure 19:
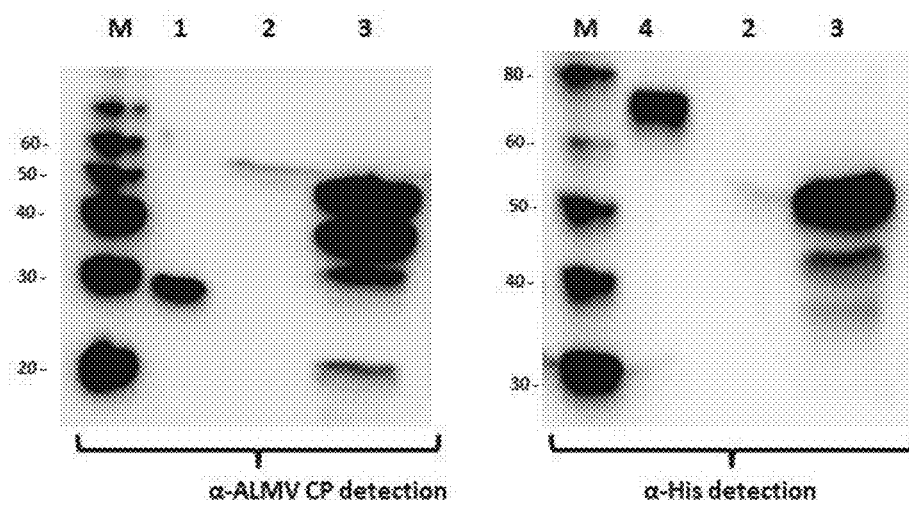

FIG. 19 shows expression of fusion protein of SEQ ID NO: 5 in extract of yeast (*Pichia pastoris*) cells analyzed by Western blots, where M—Molecular weight marker; 1—AIMV CP standard; 2—extract from non-induced yeast cells, containing CP-CP fusion; 3—extract from induced yeast cells, expressing CP-CP fusion; 4—HAI protein standard containing 6×His tag.

Figure 20:
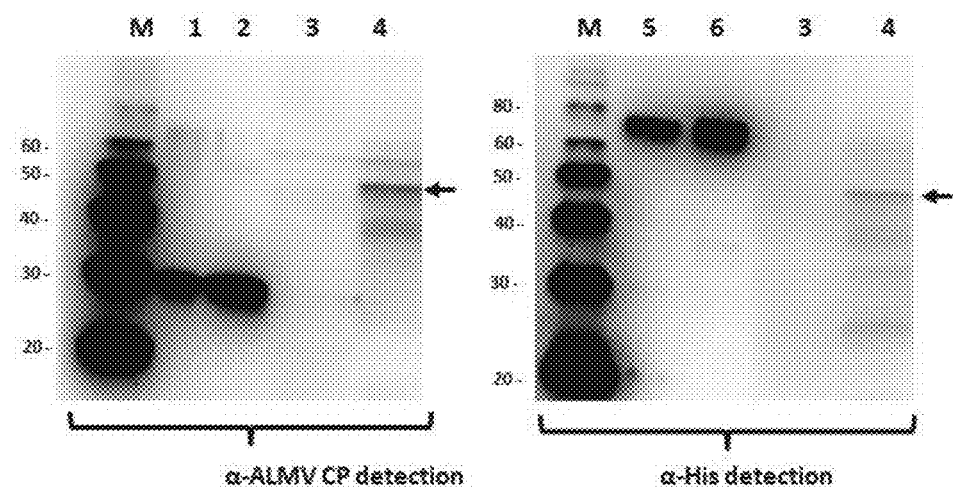

FIG. 20 shows expression of fusion protein in extract of mammalian cells analyzed Western blots, where M—Molecular weight marker; 1, 2—AIMV CP standard; 3—extract from non-transfected mammalian cells; 4—extract from transfected mammalian cells, expressing CP-CP fusion; 5, 6—HAI protein standard, containing 6×His tag. Arrow indicates band corresponding to CP-CP fusion.

Figure 21:
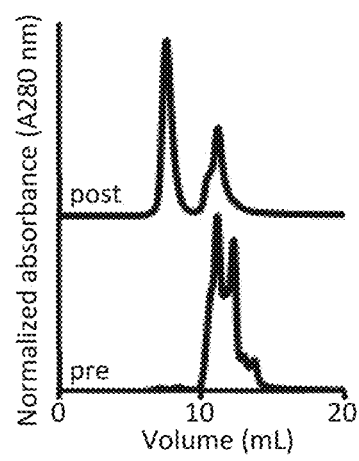

FIG. 21 shows in vitro VLP formation of a $CP^2$ fusion. A $CP^2$ fusion protein resolved on analytical size exclusion chromatography, pre and post in vitro particle formation, where virus-like particles (VLPs) resolve at ~9 mL.

Figure 22:
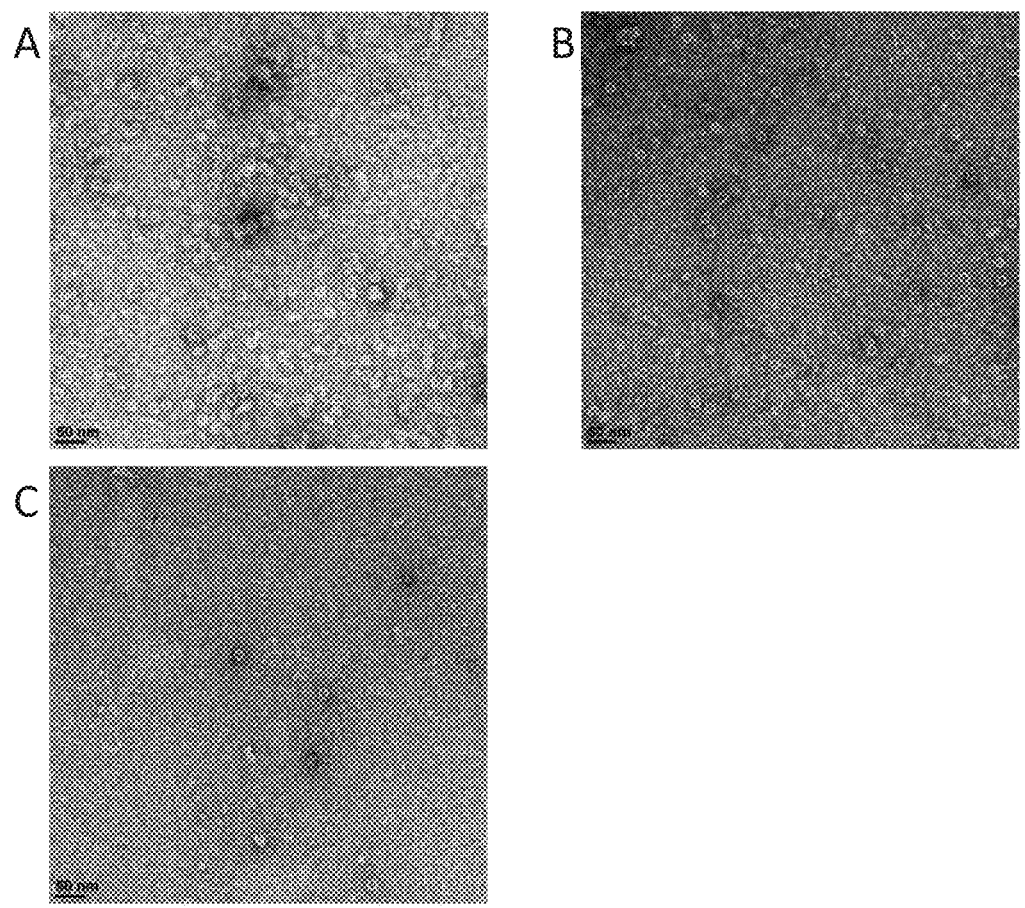

FIG. 22 shows negative stained transmission electron microscopy images of VLPs formed from CP-CP produced in (A) plant cells, (B) yeast cells, and (C) insect cells.

Figure 23:
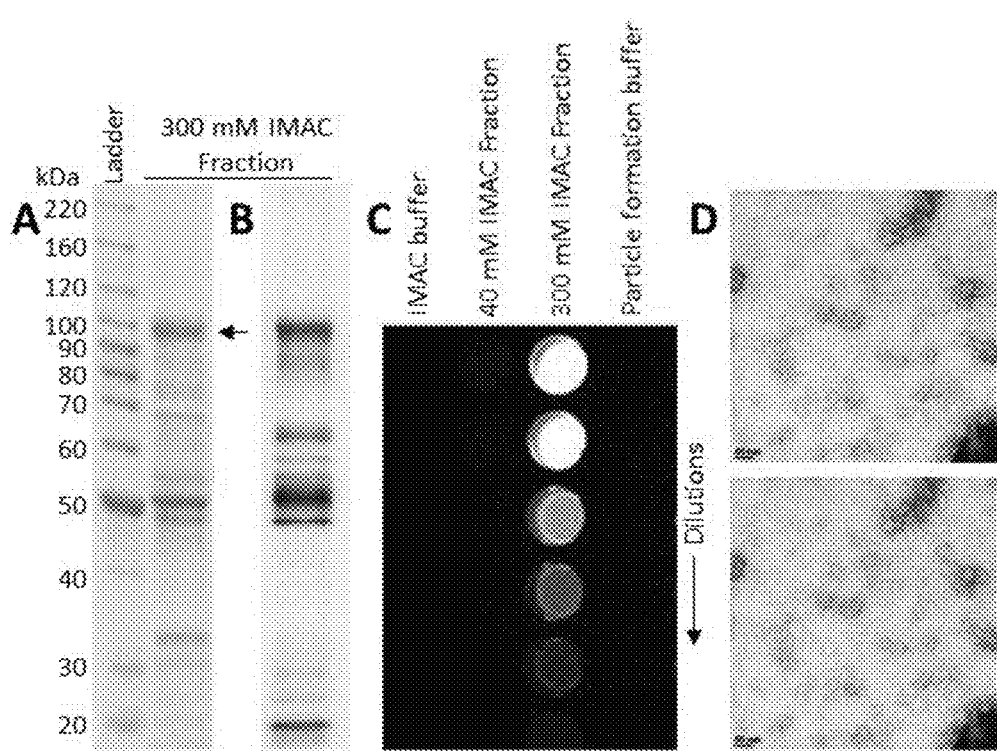

FIG. 23 shows analysis of the HRP-$CP^2$ fusion protein. The HRP-$CP^2$ fusion protein was isolated by IMAC chromatography and characterized by (A) Coomassie stained SDS-PAGE, (B) anti-His Western blot, (C) chemiluminescence assay to detect HRP activity, and D) transmission electron microscopy images.

DETAILED DESCRIPTION OF THE INVENTION

The present invention is based on the discovery that novel fusion proteins having recombinant coat proteins (CPs) derived from alfalfa mosaic virus (AIMV) proteins expressed in tandem, linked by a flexible linker to allow the AIMV molecules to align side by side, can be expressed in various expression systems and used to form virus like particles (VLPs), either in vivo or in vitro. This technology provides an effective and productive tool for making VLPs to present a wide variety of target proteins.

The present invention provides a fusion protein. The fusion protein comprises two or more recombinant coat proteins (CPs) derived from alfalfa mosaic virus (AIMV), which are referred to as recombinant AIMV CPs. The recombinant AIMV CPs may be the same or different. Two adjacent recombinant AIMV CPs may be linked via a linkage peptide. The recombinant AIMV CPs are aligned in a manner conducive to VLP formation by the fusion protein. The fusion protein may further comprise a target protein at the N-terminus of the recombinant AIMV CPs. In some embodiments, the fusion protein comprises two recombinant AIMV CPs, also referred to as CP-CP or $CP^2$.

The term "derived from" as used herein refers to an origin or source. The recombinant coat proteins (CPs) are derived from the coat protein (CP) of alfalfa mosaic virus (AIMV) (FIG. 1). The amino acid sequence of the AIMV CP is shown in FIG. 1. The recombinant AIMV CP may comprise the AIMV CP, in part or in whole, and may be a fragment or variant of the AIMV CP.

The term "mutation" as used herein refers to a deletion, insertion or substitution of one or more amino acids. An amino acid substitution may be a conservative amino acid substitution. A "conservative amino acid substitution" is one in which the amino acid residue is replaced with an amino acid residue having a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

For example, one or more trypsin sites at residues 6, 7, 11, 17, 18, 27 and/or 37 of the AIMV CP (SEQ ID NO: 1) may be mutated by, for example, a deletion, insertion or substitution. A chymotrypsin site at residue 22 of the AIMV CP (SEQ ID NO: 1) may be mutated by, for example, a deletion, insertion or substitution. One or more in planta digestion sites between residues 24 and 25, between residues 25 and 26, and/or between residues 37 and 38 of the AIMV CP (SEQ ID NO: 1) may be mutated by, for example, a deletion, insertion or substitution. Residues 17-38 of the AIMV CP (SEQ ID NO: 1) may be mutated by, for example, a deletion, insertion or substitution by a linkage peptide consisting of SEQ ID NO: 2.

The term "subject" as used herein refers to a mammal, for example, a mouse or human. Preferably, the subject is a human. The subject may be a patient suffering from a disease or condition. The subject may be in need of induction of an immunological response, treatment of a disease or condition, or detection of a biomarker.

The term "an effective amount" as used herein refers to an amount of a fusion protein, virus like particles (VLPs) formed by the fusion protein, or a composition comprising the fusion protein or the VLPs required to achieve a stated goal (e.g., induction of an immunological response, treatment of a disease or condition, detection of a biomarker or catalyzing a reaction). The effective amount of the fusion protein, the VLPs, or the composition may vary depending upon the stated goals, the physical characteristics of the subject, the nature and severity of the disease or disorder, the existence of related or unrelated medical conditions, the nature of the fusion protein, the VLPs or the composition, the means of administering the fusion protein, the VLPs or the composition to the subject, and the administration route. A specific dose for a given subject may generally be set by the judgment of a physician. The pharmaceutical composition may be administered to the subject in one or multiple doses.

A recombinant AIMV CP is a polypeptide comprising an amino acid sequence derived from that of the AIMV CP (SEQ ID NO: 1), for example, at least about 80%, 85%, 90%, 95% or 99% identical to SEQ ID NO: 1. The recombinant AIMV CP may consist of an amino acid sequence identical to SEQ ID NO: 1 except one or more mutations. For example, the recombinant AIMV CP may consist of the amino acid sequence of SEQ ID NO: 3 or 4 (FIG. 1).

A linkage peptide may be of any length permitting one or more desirable properties of the fusion protein. For example, the linkage peptide may be of a length permitting formation of a virus like particle (VLP) by the fusion protein or displaying a target protein on the surface of the VLP. The linkage peptide may have at least about 1, 5, 10, 15, 20, 25, 30, 35, 40, 45 or 50 amino acids, or about 1-50, 5-30 or 10-20 amino acids. The linkage peptide may consist of GGGGSGGGGSGGGGS (SEQ ID NO: 2).

The target protein may be an agent selected from the group consisting of an immunogenic agent, a therapeutic agent, a diagnostic agent, and an enzyme. The target protein may be an immunogenic agent. The immunogenic agent may be Malaria antigens (e.g., Pfs230 and Pfs25), influenza antigens (e.g., ectodomain and sub-domain of haemagglutinin), yellow fever subdomain, Western Equine encephalitis virus (WEE) antigen, and Eastern Equine encephalitis virus (EEE) antigen. The target protein may be a therapeutic agent. The target protein may be a diagnostic agent. The target protein may be an enzyme.

In one embodiment, the fusion protein comprises a first recombinant viral coat protein, a second recombinant viral coat protein and a first linkage peptide. The first recombinant viral coat protein is linked to N-terminus of the first linkage peptide. The second recombinant viral coat protein is linked to C-terminus of the first linkage peptide. The first recombinant viral coat protein comprises an amino acid sequence at least about 80%, 85%, 90%, 95% or 99% identical to SEQ ID NO: 1. The second recombinant viral coat protein comprises an amino acid sequence at least about 80%, 85%, 90%, 95% or 99% identical to SEQ ID NO: 1.

In another embodiment, the fusion protein comprises a target protein, a first recombinant viral coat protein, a second recombinant viral coat protein and a first linkage peptide. The target protein is at N-terminus of the first recombinant viral coat protein. The first recombinant viral coat protein is linked to N-terminus of the first linkage peptide. The second recombinant viral coat protein is linked to C-terminus of the first linkage peptide. The first recombinant viral coat protein comprises an amino acid sequence at least about 80%, 85%, 90%, 95% or 99% identical to SEQ ID NO: 1. The second recombinant viral coat protein comprises an amino acid sequence at least about 80%, 85%, 90%, 95% or 99% identical to SEQ ID NO: 1.

The first and second recombinant viral coat proteins may be aligned in a manner conducive to VLP formation by the fusion protein. The first linkage peptide may be of any length permitting formation of a virus like particle (VLP) by the fusion protein. For example, the first linkage peptide may have at least about 5, 10, 15, 20, 25, 30, 35, 40, 45 or 50 amino acids, or about 1-50, 5-30 or 10-20 amino acids. The first linkage peptide may consist of SEQ ID NO: 2.

Where the fusion protein comprises the target protein, the fusion protein may further comprise a second linkage peptide, wherein the target protein is linked to N-terminus of the second linkage peptide, and the first recombinant viral coat protein is linked to C-terminus of the second linkage peptide. The second linkage peptide may be of any length permitting display of the target protein on the surface of a VLP formed by the fusion protein. For example, the second linkage peptide may have at least about 5, 10, 15, 20, 25, 30, 35, 40, 45 or 50 amino acids, or about 1-50, 5-30 or 10-20 amino acids. The second linkage peptide may consist of SEQ ID NO: 2.

The first recombinant viral coat protein may comprise an amino acid sequence at least about 80%, 85%, 90%, 95% or 99% identical to SEQ ID NO: 1 with a mutation of one or more trypsin sites at, for example, residues 6, 7, 11, 17, 18, 27 and/or 37. The first recombinant viral coat protein may comprise an amino acid sequence at least about 80%, 85%, 90%, 95% or 99% identical to SEQ ID NO: 1 with a mutation of a chymotrypsin site at, for example, residue 22. The first recombinant viral coat protein may comprise an amino acid sequence at least about 80%, 85%, 90%, 95% or 99% identical to SEQ ID NO: 1 with a mutation of one or more in planta digestion sites, for example, between residues 24 and 25, between residues 25 and 26, and/or between residues 37 and 38.

The first recombinant viral coat protein may comprise an amino acid sequence at least about 80%, 85%, 90%, 95% or 99% identical to SEQ ID NO: 1 with a deletion, insertion or substitution at residues 17-38. For example, residues 17-38 may be substituted with a third linkage peptide. The third linkage peptide may consist of SEQ ID NO: 2. The first recombinant viral coat protein may consist of SEQ ID NO: 3. The first recombinant viral coat protein may further comprise a mutation of one or more trypsin sites at, for example, residues 6, 7 and/or 11.

The second recombinant viral coat protein may comprise an amino acid sequence at least about 80%, 85%, 90%, 95% or 99% identical to SEQ ID NO: 1 with a mutation of one or more trypsin sites at, for example, residues 6, 7, 11, 17, 18, 27 and/or 37. The second recombinant viral coat protein may comprise an amino acid sequence at least about 80%, 85%, 90%, 95% or 99% identical to SEQ ID NO: 1 with a mutation of a chymotrypsin site at, for example, residue 22. The second recombinant viral coat protein may comprise an amino acid sequence at least about 80%, 85%, 90%, 95% or 99% identical to SEQ ID NO: 1 with a mutation of one or more in planta digestion sites, for example, between residues 24 and 25, between residues 25 and 26, and/or between residues 37 and 38.

The second recombinant viral coat protein may comprise an amino acid sequence at least about 80%, 85%, 90%, 95% or 99% identical to SEQ ID NO: 1 with a deletion, insertion or substitution at residues 17-38. The second recombinant viral coat protein may consist of SEQ ID NO: 4. Residues 17-38 of SEQ ID NO: 1 may be substituted with a fourth linkage peptide. The fourth linkage peptide may be of any length, for example, having at least about 1, 5, 10, 15, 20, 25, 30, 35, 40, 45 or 50 amino acids. The fourth linkage peptide may consist of SEQ ID NO: 2. The second recombinant viral coat protein may further comprise a mutation of one or more trypsin sites at, for example, residues 6, 7 and/or 11.

In one embodiment, the fusion protein comprises SEQ ID NO: 5. In another embodiment, the fusion protein consists of SEQ ID NO: 5.

For each fusion protein, a method for producing the fusion protein is provided. The method comprises introducing a nucleic acid molecule into cells, wherein the nucleic acid molecule encodes the fusion protein, and expressing the fusion protein in the cells. Thereby, the fusion protein is produced. The nucleic acid molecule may be introduced into the cells transiently or stably. The method may further comprise purifying the fusion protein from the cells. The cells may be any cells in which the fusion protein can be expressed. The cells may be in a plant or a portion of a plant. The cells may be yeast cells. The cells may be insect cells. The cells may be mammalian cells.

For each fusion protein, a composition comprising the fusion protein is provided. The composition may further comprise a pharmaceutically acceptable excipient. The pharmaceutically acceptable excipient may be an adjuvant.

A virus like particle (VLP) formed by the fusion protein of the present invention is provided. Where the fusion comprises a target protein, the target protein is displayed on the surface the VLP. The VLP may be formed in a cell, an organism or a portion of an organism. The cell may be selected from the group consisting of a plant cell, a yeast cell, an insect cell and a mammalian cell. The cell may be in a plant or a portion thereof. The plant may be a *Nicotiana* species. The *Nicotiana* species may be selected from the group consisting of *Nicotiana benthamiana* and *Nicotiana tabacum*. The cell may be a yeast cell. The cell may be an insect cell. The cell may be a mammalian cell.

A composition comprising the virus like particles (VLPs) of the present invention is provided. At least about 50%, 60%, 70%, 80%, 90%, 95% or 99% of the VLPs may have a diameter within less than about 50%, 40%, 30%, 20%, 10% or 5% of an average diameter of the VLPs. The composition may further comprise a pharmaceutically acceptable excipient. The pharmaceutically acceptable excipient may be an adjuvant.

A method of producing virus like particles (VLPs) is provided. The method comprises introducing a nucleic acid molecule into a cell, an organism or a portion of the organism, wherein the nucleic acid molecule encodes the fusion protein of the present invention, expressing the fusion protein in the cell, the organism or the portion of the organism, and forming virus like particles by the fusion protein. Thereby, the VLPs are produced. The nucleic acid molecule may be introduced transiently or stably into the cell, the organism or the portion of the organism. Where the fusion protein comprises a target protein, the target protein is displayed on the surface of the VLPs. At least about 50%, 60%, 70%, 80%, 90%, 95% or 99% of the VLPs may have a diameter within less than about 50%, 40%, 30%, 20%, 10% or 5% of an average diameter of the VLPs. The VLPs may be formed by at least about 50%, 60%, 70%, 80%, 90% or 95% of the fusion protein.

Where the VLPs are formed in the cell, the organism or the portion of the organism, the method may further comprise purifying the VLPs from the cell, the organism or the portion of the organism.

Where the VLPs are not formed inside the cell, the organism or the portion of the organism, the method may further comprise purifying the fusion protein from the cell, the organism or the portion of the organism before the VLPs are formed.

A method of inducing an immunological response in a subject is provided. The method comprises administering to the subject an effective amount of a fusion protein comprising an immunogenic agent as the target protein according to the present invention or VLPs formed by the fusion protein. The subject may be a patient in need of the induction of the immunological response.

A method of treating a disease or condition in a subject is provided. The method comprises administering to the subject an effective amount of a fusion protein comprising a therapeutic agent as the target protein according to the present invention or VLPs formed by the fusion protein. The subject may be a patient who suffers from the disease and condition.

A method of detecting a biomarker in a sample from a subject is provided. The method comprises contacting the sample with an effective amount of a fusion protein comprising a diagnostic agent as the target protein according to the present invention or VLPs formed by the fusion protein.

The diagnostic agent binds the biomarker. The biomarker may be an indicator of a disease or condition from which the subject is suspected of suffering.

A method of catalyzing a reaction by a reagent is provided. The method comprises contacting the reagent with an effective amount of a fusion protein comprising an enzyme as the target protein according to the present invention or VLPs formed by the fusion protein. The enzyme catalyzes the reaction. The reaction may be catalyzed in vitro or in vivo.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

Example 1. Antibodies to Plant-Produced *P. falciparum* Sexual Stage Proteins Exhibit Transmission Blocking Activity Transmission blocking vaccines (TBV) are considered a critical component in the overall strategy for control and eventually elimination of malaria worldwide. Sexual-stage proteins expressed by *Plasmodium falciparum*, Pfs230 and Pfs25, are the main transmission blocking antigens moving through clinical trial development. Antibodies generated upon vaccination with either of these results in interruption of sporogonic development in the mosquito, and transmission to the next host. Using a plant based transient expression system, we have produced Pfs25 and Pfs230 fused to various carrier proteins in *Nicotiana benthamiana*, purified and characterized the proteins, and evaluated the vaccine candidates in animal models for generation of transmission reducing activity (TRA)/transmission blocking activity (TBA). The Pfs25 and Pfs230 vaccine candidates are expressed at high levels, and induced TBA that persist up to 6 months post immunization. These data demonstrate the potential of the new malaria vaccine candidates, and supports the feasibility of expressing *Plasmodium* antigens in a plant-based system.

The incidents of malaria have declined over the last half decade, with an estimated reduction of 50-75% in endemic areas (2015 WHO World Malaria Report). The combined use of mosquito nets, artemisinin based therapies, and residual spraying have reduced malaria related deaths down to an estimated 400,000 deaths in 2015. These tools and a malaria vaccine, RTS,S/ASO1, are considered key interventions to reach the newly set goal of a 90% reduction in malaria mortality rates by 2030. Additional therapeutic vaccines that focus on breaking the cycle of parasite transmission, such as transmission-blocking vaccines, are also considered key areas of importance.

These alternative vaccines reduce or block transmission of the malaria parasite from the mosquito to the person and will play an important role in reducing transmission burden in highly endemic areas. The leading transmission blocking antigens are Pfs25 and Pfs230. Pfs25 is not expressed by the parasite when it is in the human host, and as such the immune response is completely driven by active immunization. Alternatively, Pfs230 is expressed by the parasite when it is in the human host during blood stage infection, and thus its immunogenicity is naturally boosted and maintained during the infection cycles. Pre-clinical animal studies have shown that immunization with Pfs230 candidates generate TBA and non-immunized convalescent malaria patients have naturally acquired anti-Pfs230 antibodies.

Pfs230 Construct Designs

Pfs230 primary sequence schematic (FIG. 2). Cysteine motif (CM) domains are essentially as described by Williamson et al (1995) Mol Biochem Parasitol, 75(1): 33-42. The amino terminus portion (444-730) was expressed with a carboxyl terminal 6×His tag and KDEL sequence (Pfs230-AM). One putative N-Linked glycosylation site was mutated (N→Q). The Pfs230-AM sequence was also expressed as a fusion to the amino terminus Alfalfa Mosaic Virus coat protein (CP). This construct was unstable, leading to Pfs230 antigen degradation. A novel design was generated where the Pfs230-AM molecule is fused to the amino terminus of a tandem CP-CP fusion where the CPs are spaced with a flexible linker. This construct, Pfs230-$CP^2$, self-assembled into a virus like particle (VLP) and displayed the Pfs230 antigen on the VLPs surface with minimal Pfs230 degradation.

Purification and Characterization of Pfs230-$CP^2$ VLPs

The Pfs230-$CP^2$ DNA sequence was cloned into plant expression vectors, and infiltrated into plants. After four days of incubation, the plants were harvested, homogenized, and the Pfs230-$CP^2$ VLPs purified by IMAC chromatography, followed by a particle formation step where the Pfs230-$CP^2$ protein self-assemble into the VLPs (FIGS. 4A and B). The non-covalently linked peptides show two main protein bands on SDS-PAGE and are recognized in Western blot by anti-His and two anti-Pfs230 monoclonal antibodies (mAb) 2G5 and 2610 (FIG. 3). Negative stained transmission electron microscopy shows the anticipated VLP shaped particles (FIG. 4B), that elute from SEC at the anticipate size of ~2 M Dalton (FIG. 4A).

Pfs230 Animal Study Design

The Pfs230 vaccine candidate Pfs230-$CP^2$ VLP was tested in a preliminary rabbit immunogenicity study. Five rabbits were immunized with 10 µg of Pfs230 at days 0 and 28 (Table 1).

TABLE 1

Rabbit immunogenicity study design.

| Rabbit # | Vaccine | Route | Adjuvant | Pfs230 dose (µg) at day 0 and 28 |
|---|---|---|---|---|
| 5 | Pfs230-$CP^2$ VLP | IM | Alhydrogel | 10 |

Transmission Blocking Activity of Immunized Serum

Serum was taken at 56 days post immunization and tested in an ex vivo standard membrane feeding assay (SMFA) to examine transmission blocking activity of immunized rabbit sera. Purified immunoglobulin (IgG) was combined (final concentration 3.75 mg/mL) with the gametocyte containing blood meal fed to mosquitos. The anti-Pfs25 mAb 4B7 was used as a positive control. The Pfs230-$CP^2$ vaccine candidate resulted in high levels of transmission blocking activity in the serum of immunized rabbits (Table 2).

TABLE 2

SMFA results from rabbits immunized
with Pfs230-CP² vaccine candidate.

| Sample name | Average oocyts | % inhibition estimate | 95% CI Lo | 95% CI Hi | p-value |
|---|---|---|---|---|---|
| mAb-4B7 control | 3.0 | 93.8 | 85.6 | 97.3 | 0.001 |
| Pfs230-CP² | 0.0 | 100.0 | 98.8 | 100.0 | 0.001 |
| VLP | 0.1 | 99.7 | 99.0 | 100.0 | 0.001 |
|  | 0.1 | 99.7 | 99.0 | 100.0 | 0.001 |
|  | 0.2 | 99.6 | 98.7 | 100.0 | 0.001 |
|  | 0.0 | 100.0 | 99.7 | 100.0 | 0.001 |

Example 2. Other Examples of Application of the CP-CP Format

Malaria Pfs25 Antigen

Figure 2:
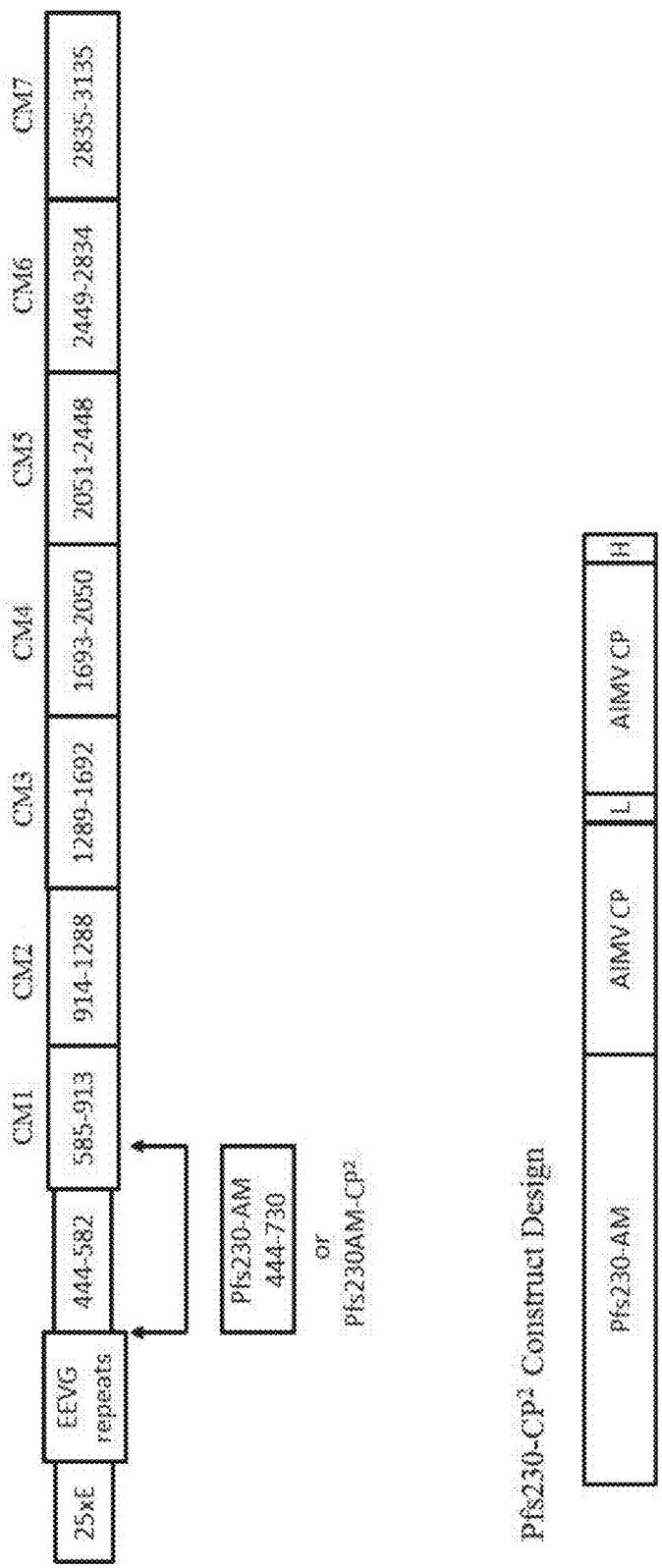
FIG. 2 shows a schematic of the Pfs230 protein, highlighting the region of the protein displayed on a VLP (Pfs230-$CP^2$).
Figure 3:
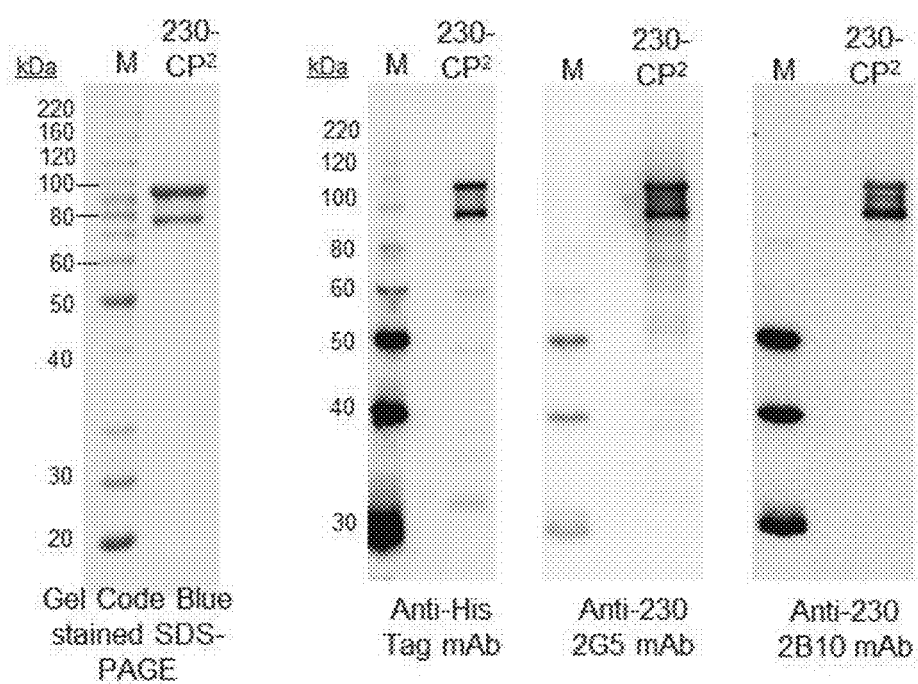
FIG. 3 shows electrophoretic characterization of Pfs230-$CP^2$. The protein is analyzed by gel code Blue stained SDS-PAGE, and recognized by anti-His tag mAb, anti-230 2G5 mAb, and anti-230 2B10 mAb.
Figure 4:
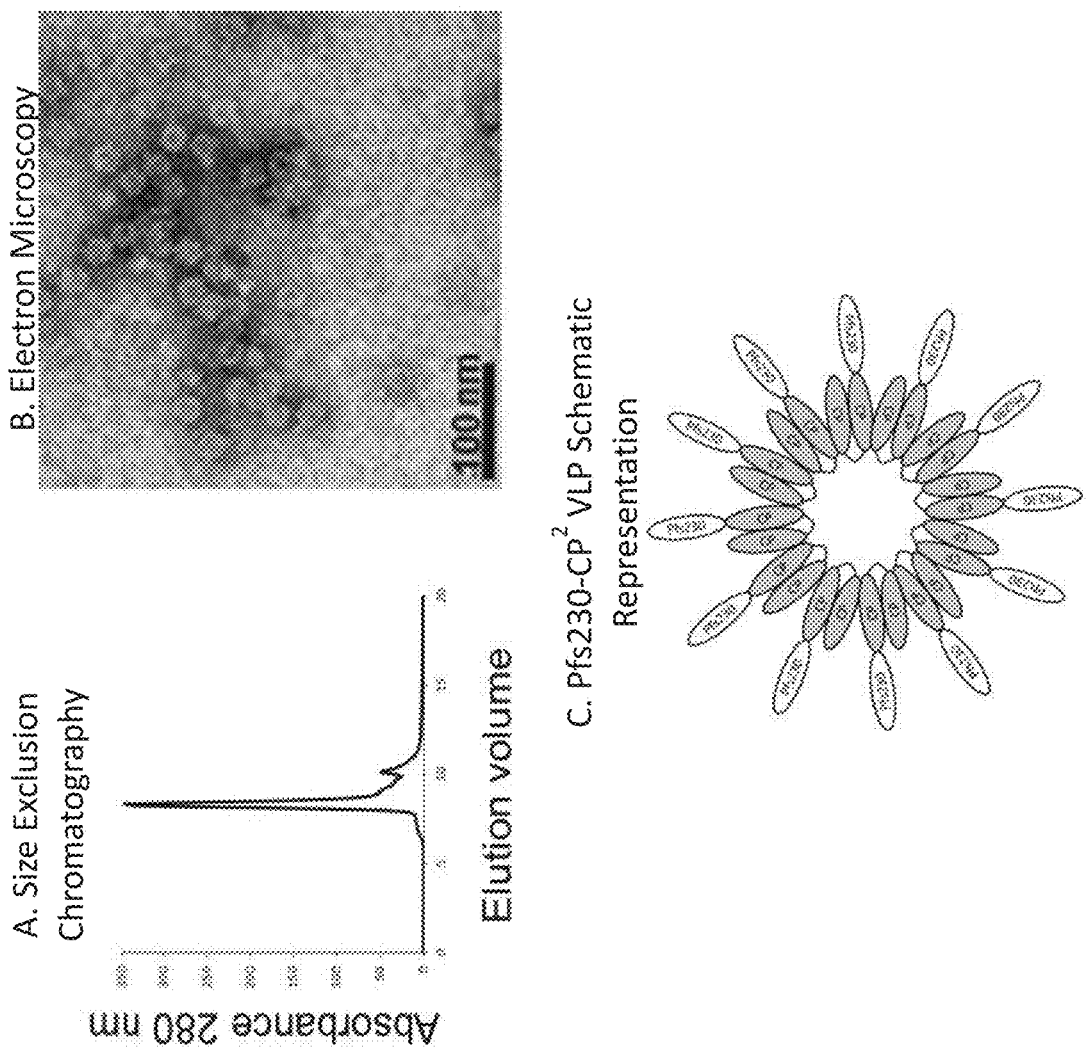
FIG. 4 shows characterization of the Pfs230-$CP^2$ fusion protein as a virus-like particle. (A) Analytical size exclusion chromatography analysis. (B) Negatively stained transmission electron microscopy image of purified Pfs230-$CP^2$ VLPs. (C) Cartoon image of the Pfs230-$CP^2$ VLPs showing the levels of antigen display.
Figure 5:
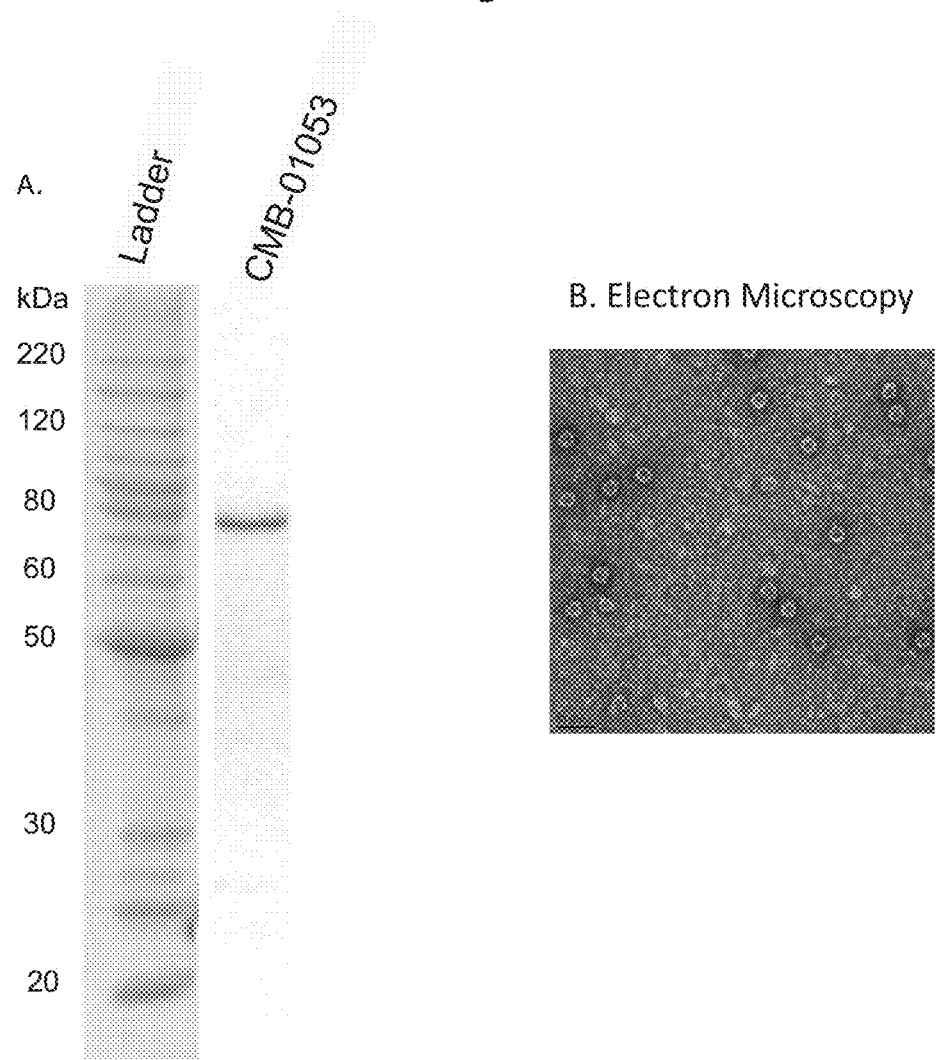
FIG. 5 shows characterization of the Pfs25 protein as a $CP^2$ fusion protein. (A) Gel code Blue stained SDS-PAGE of Pfs25-$CP^2$ protein CMB-01053, and (B) Negatively stained transmission electron microscopy image of CMB-01053 displaying the Pfs25 protein on VLPs.

The malaria Pfs25 antigen was expressed as a $CP^2$ fusion (CMB-01053) resulting in a single polypeptide, which self-assembled into VLP particles (FIG. 5). By contrast, when a single CP fusion was expressed, the protein had high levels of cleavage, resulting in lower than anticipated decoration of Pfs25.

Influenza Antigens—H1 Subtype

Figure 6:
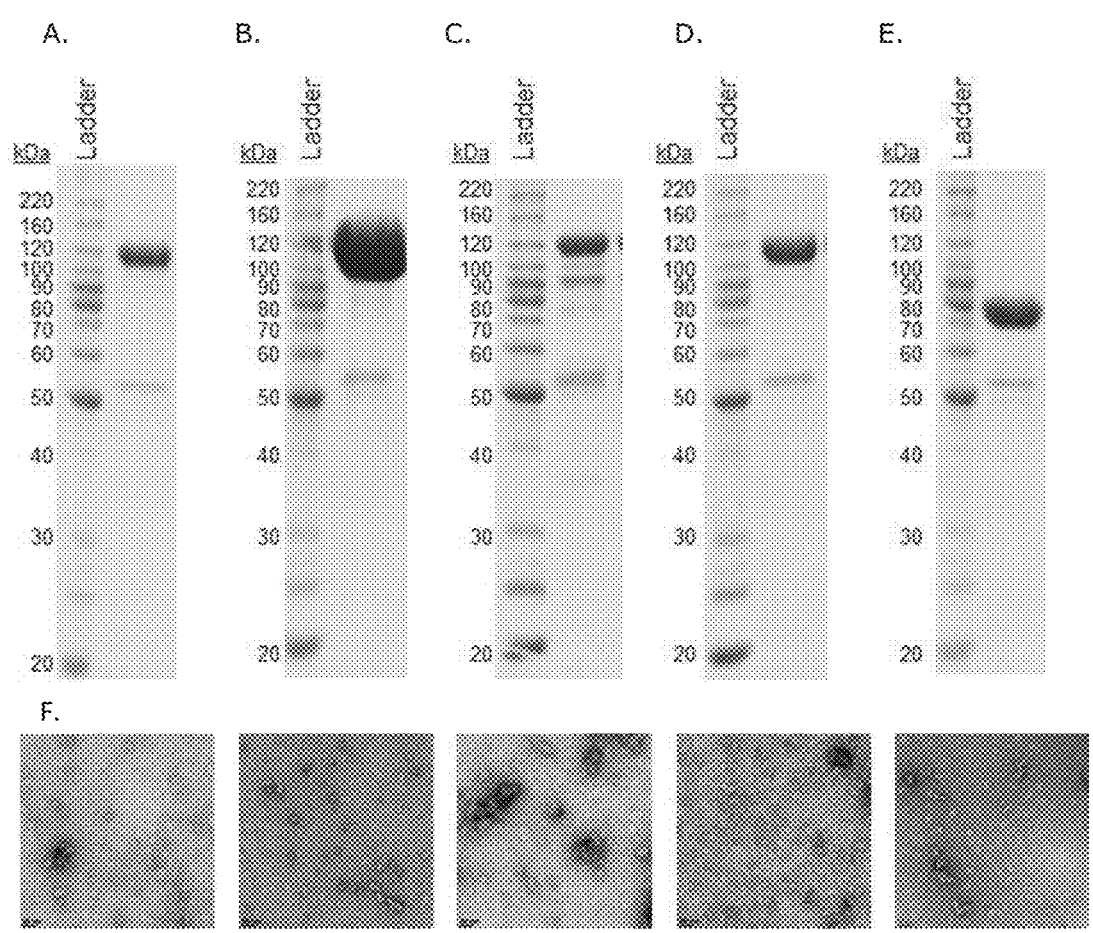
FIG. 6 shows gel code Blue stained SDS-PAGE of $CP^2$ displayed antigens, (A) H1 influenza $CP^2$ fusion protein CMB-02039, (B) H3 influenza $CP^2$ fusion protein CMB-02079, (C) H5 influenza $CP^2$ fusion protein CMB-02011, (D) H7 influenza $CP^2$ fusion protein CMB-02059 or (E) H1 influenza protein domain $CP^2$ fusion protein CMB-02047 after primary column purification. (F) Negatively stained transmission electron microscopy images of (left to right)

The ectodomain of haemagglutinin was expressed as a $CP^2$ fusion resulting in a stable recombinant protein (FIG. 6A). Construct code: CMB-02039. The influenza $CP^2$ constructs showed better expression and recovery compared to the single CP fusions.

Influenza Antigens—H3 Subtype

The ectodomain of haemagglutinin was expressed as a $CP^2$ fusion resulting in a stable recombinant protein (FIG. 6B). Construct code: CMB-02079. The influenza $CP^2$ constructs showed better expression and recovery compared to the single CP fusions.

Influenza Antigens—H5 Subtype

The ectodomain of haemagglutinin was expressed as a $CP^2$ fusion resulting in a stable recombinant protein (FIG. 6C). Construct code: CMB-02011. The influenza $CP^2$ constructs showed better expression and recovery compared to the single CP fusions.

Influenza Antigens—H7 Subtype

The ectodomain of haemagglutinin was expressed as a $CP^2$ fusion resulting in a stable recombinant protein (FIG. 6D). Construct code: CMB-02059. The influenza $CP^2$ constructs showed better expression and recovery compared to the single CP fusions.

Influenza Antigens—H1 Subtype

Sub-domain of haemagglutinin (HA3) was expressed as a $CP^2$ fusion resulting in a stable recombinant protein (FIG. 6E). Construct code: CMB-02047. The influenza $CP^2$ constructs showed better expression and recovery compared to the single CP fusions.

Western Equine Encephalitis Virus (EEV) Antigen

A sub-domain of the Western strain of EEV E2 glycoprotein was expressed as a $CP^2$ fusion resulting in a stable recombinant protein (FIG. 7). Construct code: CMB-02412. These constructs were either poorly or not expressible as single CP fusions.

Eastern Equine Encephalitis Virus (EEV) Antigen

A sub-domain of the Eastern strain of EEV E2 glycoprotein was expressed as a $CP^2$ fusion resulting in a stable recombinant protein (FIG. 8). Construct code: CMB-02383. These constructs were either poorly or not expressible as single CP fusions.

Eastern Equine Encephalitis Virus (EEV) Antigen

The ectodomain of the Eastern strain of EEV E2 glycoprotein was expressed as a $CP^2$ fusion resulting in a stable recombinant protein (FIG. 9). Construct code: CMB-02380. These constructs were either poorly or not expressible as single CP fusions.

Example 3. First Generation VLP

To increase the immunogenicity of the malaria transmission blocking Pfs25 vaccine antigen, the antigen was displayed on a VLP, by fusion to the amino terminus of the alfalfa mosaic virus (A/MV) coat protein (CP) (FIG. 10A). This first generation Pfs25-VLP was called A85, and was shown to form stable VLPs, be highly immunogenic, and effective at preventing the transmission of malaria in animal models. This molecule was tested through a Phase 1 clinical trial, where it showed no adverse reactivity. However, the VLPs effectiveness was hampered by in planta cleavage events within the CP molecule, resulting in considerable loss of the Pfs25 antigen from the VLP (FIG. 10B-C).

Example 4. Second Generation VLPs

To address this antigen loss, work was performed to identify the sites of cleavage within the CP molecule. Amino terminal sequencing was performed, and the sites of CP cleavage were identified to be at positions 24 and 36 of the CP molecule. A third possible A/MV CP cleavage site was identified in the published literature at position 26.

Three different versions of the CP molecule were generated to prevent CP degradation, and to increase the antigen display on the VLP (FIG. 11).

B29 The three identified cleavage sites were point mutated to alanine.

B30 The 22-amino acid region containing the sites of degradation was removed, generating a shorter d22CP molecule.

B64 The 22-amino acid region containing the sites of degradation was replaced with a flexible linker (FL1), comprised of the amino acids GGGGSGGGGSGGGGSGG.

The constructs B30 and B64 had much higher protein recovery, and were purified as a single protein without degradation. However, these molecules did not form VLPs. The purified B29 protein had some protein degradation, but could successfully form VLPs. Compared to the original A85 molecule, the B29 molecule had more Pfs25 antigens displayed per VLP, resulting in improved immunogenicity and malaria transmission blocking ability.

From this work, it was determined that

1. It was possible to improve the antigen display on the VLP through protein design of the CP molecule.
2. The identified 22-amino acid region contained all the in planta CP molecule cleavage sites.
3. If the protein was just an antigen-CP fusion protein, such as B30 or B64, it may not form VLPs. However, if there was additional antigen free CP present, through for example, internal cleavage of the antigen-CP fusion protein, then VLP formation was possible.

Example 5. Third Generation VLPs

Eight different 3rd-generation VLP constructs were developed to further improve antigen display on the VLP (FIG. 12).

CMB-01045 The B64 molecule was modified to replace the FL1 with a longer flexible linker (FL2) comprised of the amino acids GGGGSAAAL-GAAGGGGSAAGTSAAGGGGSAAALGAA CMB-01047 The first 27-amino acids of the CP molecule were removed and replaced with the FL2 linker.

CMB-01049 The B64 molecule was modified to replace the FL1 with an alpha helical linker (AH) comprised of the amino acids EAAAKEAAAKEAAAKEAAAKEAAAKEAAAK CMB-01075 The B64 molecule was modified by the addition of a Kex2P self-cleavage site after the FL1. The Kex2P site contained the amino acids IGKR-GIGKRGIGKRG CMB-01053 The B64 molecule was modified by the addition of a second FL1 and d22CP to the C-terminus of the molecule as described in Example 2 (FIG. 5).

CMB-01063 The CMB-01045 molecule was modified by the addition of a second FL1 and d22CP to the C-terminus of the molecule.

CMB-01067 The B64 molecule was modified by the addition of a second d22CP and FL1 to the N-terminus of the molecule.

CMB-01071 The B64 molecule was modified by the addition of a second d22CP and FL2 to the N-terminus of the molecule.

The constructs CMB-01047, CMB-01075, CMB-01067, and CMB-01071 produce very low levels of protein, thereby preventing analysis of fusion to total protein ratios, or particle formation. The constructs CMB-01045 and CMB-01049 produced protein, but limited amounts of VLPs. The two $CP^2$ VLP molecules, CMB-01053 and CMB-01063 both produced protein, which formed into VLPs, with the CMB-01053 molecule having the highest expression. The CMB-01053 protein was purified as a single protein without degradation (FIG. 13A). Compared to the original A85 VLP, this newly developed molecule allowed for much higher levels of protein production and formed VLPs with greatly improved antigen display (FIG. 13B-C).

Three of the Pfs25 molecules were compared in a mouse animal study. The CMB-01053 VLP was compared to both the B30 molecule and the B29 VLP over a range of low Pfs25 antigen doses (FIG. 14A). The proteins were administered intramuscularly with alhydrogel adjuvant. At day 56 of the study (FIG. 14B), the anti-Pfs25 IgG titers of the B30 group was significantly lower than the IgG titers from either B29 or CMB-01053 VLP ($p<0.05$) at the 0.003 μg dose level. At day 168 of the study (FIG. 14C), the B30 group at a 0.003 μg dose had significantly lower anti-Pfs25 IgG titers than the B29 group ($p<0.05$), while at the 0.03 μg Pfs25 dose level the CMB-01053 group had significantly higher anti-Pfs25 IgG titers than the B29 VLP group ($p<0.01$). This is consistent with the CMB-01053 VLP not just displaying more Pfs25 antigens per molecule, but also displaying the antigens more effectively. Statistics were performed using Kruskal-Wallis analysis followed by Dunn's multiple comparison test, with *=$p<0.05$ and **=$p<0.01$.

To determine if the molecules have transmission blocking activity, serum was collected at days 56 and 168 post immunization and analyzed in an ex vivo standard membrane feeding assay (SMFA). All three Pfs25 molecules, including the CMB-01053 VLP, demonstrated malaria transmission blocking activity (FIG. 14D), with only the B30 group at the 0.003 μg dose show a statistically significant difference in SMFA levels, $p<0.0001$ at day 56, and $p<0.05$ at day 168. Statistics were performed using a one-way ANOVA followed by Tukey's multiple comparison test.

Additional antigens were tested on the $CP^2$ design developed for CMB-01053. Antigens successfully displayed on the $CP^2$VLP include the malaria antigen Pfs230, a yellow fever antigen, several influenza antigens, and an Eastern equine encephalitis virus antigen (FIG. 15).

Example 6. Degradation Sites in the N-Terminus of AIMV

The in silico digestion analysis for trypsin and chymotrypsin sensitive sites was performed using the program "PeptideCutter" at ExPASy, the SIB Bioinformatics Resources Portal. In planta cleavage sites of AIMV were identified from purified AIMV particles using N-terminal sequencing.

Potential sites of degradation in the N-terminus of the AIMV protein were identified using the program PeptideCutter (FIG. 16A), revealing many potential trypsin and chymotrypsin sensitive sites.

AIMV particles were purified and N-terminally sequenced, identifying sites where the AIMV protein is cleaved in planta (FIG. 16B). Information from the N-terminal sequencing and in silico digestion was used to identify the amino acids within the AIMV molecule to replace with the flexible linker. This modified AIMV sequence has a greatly reduced number of protease sensitive sites (FIG. 16C).

Example 7. Expression of Fusion Proteins in Insect Cells, Yeast Cells, and Mammalian Cells A fusion protein consisting of SEQ ID NO: 5 was expressed in insect cells (FIGS. 17 and 18), yeast cells (FIG. 19), and mammalian cells (FIG. 20) using the methods described below. All expressed fusion proteins formed or are expected to form virus-like particles.

Baculoviral Expression System.

The gene encoding a CP-CP fusion protein was optimized for expression in insect cells and synthetized by GeneArt (ThermoFisher Scientific). The gene was subcloned into BamHI/HindIII-digested baculovirus transfer vector pFastBacl (ThermoFisher Scientific) and the subcloned sequence was verified. The virus was subsequently propagated using the Bac-to-Bac Baculovirus Expression System according to the manufacturer's protocol. Briefly, the resulting vector carrying the $CP^2$ gene was transformed into E. coli DH10Bac cells containing the baculovirus genome (bacmid DNA). Transposition occurred between pFastBacl and the bacmid to generate a recombinant bacmid with $CP^2$ gene. Positive clones were selected and the recombinant bacmid was isolated and transfected into Spodoptera frugiperda (Sf21) cells for propagation of recombinant baculovirus.

For large-scale expression of $CP^2$ protein, Sf21 cells were infected at $5\times10^6$ cells/mL with virus at an optimal multiplicity of infection (MOI) of 2.5 in Sf-900™ II SFM cell medium and incubated at 27° C. with mixing at 160 rpm. Forty-eight hours post-infection, the insect cells were collected by centrifugation at 500×g for 10 minutes, after which the cells were solubilized in 100 mM pyrophosphate buffer, pH6.5, sonicated and clarified by centrifugation at 20,000×g for 20 minutes to remove cell debris. Supernatant was centrifuged at 60,000 RPMs in Ti70 rotor for two hours. Pellet was dissolved in 100 mM pyrophosphate buffer, pH6.5 and submitted for TEM.

Yeast Expression System.

The gene encoding a $CP^2$ fusion protein was optimized for expression in yeast cells and synthetized by GeneArt (ThermoFisher Scientific). The gene was subcloned into BamHI/EcoRI-digested yeast vector pPIC3.5 (ThermoFisher Scientific) and the subcloned sequence was verified. The recombinant plasmid was linearized with SalI and then transformed into *Pichia pastoris* GS115 by electroporation. The transformants were plated on MD (minimal dextrose) plates without histidine and incubated at 30° C. for 2-3 days. Colonies were analyzed by PCR, using gene specific primers. Positive colonies were propagated and fusion protein expression was induced with methanol.

Mammalian Expression System.

The gene encoding a $CP^2$ fusion protein was optimized for expression in mammalian cells and synthetized by GeneArt (ThermoFisher Scientific). The gene was subcloned into HindIII/XhoI-digested yeast vector pcDNA3.1 (ThermoFisher Scientific) and sequence verified. Plasmid DNA was used for transfection of Vero cells using LIPOFECTAMINE™ 2000. After two days of incubation cells were precipitated by centrifugation at 1000 g for 5 minutes.

Western Blot Analysis and TEM.

To characterize expression of a fusion protein in mammalian, insect or yeast cells, cells were disrupted by boiling for 10 minutes in 1× Laemmli sample buffer, when protein samples were separated on a 10% SDS-PAGE gel, transferred onto a polyvinylidene difluoride membrane, and probed with a mouse anti tetra-His mAb (Qiagen) or rabbit anti-AIMV CP polyclonal antibodies (Fraunhofer). HRP-conjugated rabbit anti-mouse or goat anti-rabbit Abs were used as secondary antibodies, respectively.

Particle formation was evaluated by negative stained transmission electron microscopy. The images of the negatively stained particles were captured using a Zeiss LIBRA 120 transmission electron microscope.

Example 8. In Vitro Particle Formation

An antigen-$CP^2$ fusion protein was purified using IMAC chromatography, and the eluted protein was concentrated using centrifugal spin concentrators to ~10 mg/mL. Analytical size exclusion chromatography was performed using an SRT-1000 column (Sepax) at 1 mL/min. In vitro particle formation was performed by dialysis of concentrated protein into 80 mM sodium pyrophosphate buffer pH 6.0.

To show that it is possible to form AIMV based VLPs in vitro, an antigen-$CP^2$ fusion protein was expressed in plants and purified by IMAC chromatography. The eluted protein was concentrated, and in vitro particle formation performed by dialysis into 80 mM sodium pyrophosphate buffer pH 6.0. Protein samples pre and post particle formation were analyzed for the presence of VLPs by analytical size exclusion chromatography, where VLPs resolve at ~9 mL (FIG. 21). No VLP associated peak was observed in the pre particle formation conditions, but a clear VLP associated peak was observed in the post particle formation conditions, confirming the in vitro formation of VLPs.

Example 9. Particle Formation from CP-CP Produced in Multiple Protein Production Systems The $CP^2$ fusion protein without an attached antigen was expressed in plants (*Nicotiana benthamiana*), yeast (*Pichia pastoris*), and insect cells (*Spodoptera frugiperda*), and purified using IMAC chromatography. The eluted protein was concentrated using centrifugal spin concentrators, and formed into particles by dialysis into 80 mM sodium pyrophosphate buffer pH 6.0. Particle formation was confirmed by negative stained transmission electron microscopy analysis.

The $CP^2$ fusion protein was successfully expressed and purified from plant, yeast, and insect protein expression systems. To confirm that the protein produced in the different expression systems could successfully form into particles, the IMAC elution's were concentrated, and formed into particles by buffer exchange into 80 mM sodium pyrophosphate buffer pH 6.0. Negatively stained transmission electron microscopy analysis confirmed the presence of particles (FIG. 22A-C).

Example 10. Enzyme Display on a $CP^2$ Molecule

In addition to displaying antigens, the $CP^2$ molecule can also display other types of proteins, such as enzymes. Horseradish peroxidase C1 (HRP) (EC number 1.11.1.7) uses hydrogen peroxide to oxidize both organic and inorganic compounds. The HRP protein was fused to the N-terminus of the $CP^2$ molecule, generating HRP-$CP^2$ fusion protein CMB-03057, and expressed in plants. The protein was isolated using IMAC chromatography against a C-terminal His-tag.

The presence of the HRP-$CP^2$ fusion protein in the 300 mM imidazole IMAC fraction was detected using Coomassie stained SDS-PAGE (FIG. 23A), and confirmed by Western blotting against the C-terminal His-tag (FIG. 23B). The samples were analyzed for HRP activity using a chemiluminescence assay, where protein fractions and buffers were incubated with HRP substrate, and light emission detected using a GeneGnome HR camera (Syngene) (FIG. 23C). Only the 300 mM imidazole IMAC fraction, containing the HRP-$CP^2$ fusion protein, displayed HRP activity, confirming both that the HRP-$CP^2$ fusion protein was produced and that the enzyme was correctly folded as a functional enzyme. The HRP-$CP^2$ sample was analyzed by negative stained transmission electron microscopy, which confirmed the presence of particles (FIG. 23D).

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

We claim:

1. A fusion protein comprising a target protein, a first recombinant viral coat protein, a second recombinant viral coat protein and a first linkage peptide, wherein the target protein is at N-terminus of the first recombinant viral coat protein, wherein the first recombinant viral coat protein is linked to N-terminus of the first linkage peptide, wherein the second recombinant viral coat protein is linked to C-terminus of the first linkage peptide, wherein the first recombinant viral coat protein comprises an amino acid sequence at least 80% identical to SEQ ID NO: 1, and wherein the second recombinant viral coat protein comprises an amino acid sequence at least 80% identical to SEQ ID NO: 1.

2. The fusion protein of claim 1, wherein the fusion protein comprises SEQ ID NO: 5.

3. The fusion protein of claim 1, wherein the target protein is an agent selected from the group consisting of an immunogenic agent, a therapeutic agent, a diagnostic agent and an enzyme.

4. The fusion protein of claim 1, wherein the target protein is an immunogenic agent.

5. The fusion protein of claim 1, wherein the target protein is a therapeutic agent.

6. The fusion protein of claim 1, wherein the target protein is a diagnostic agent.

7. The fusion protein of claim 1, wherein the target protein is an enzyme.

8. A method for producing the fusion protein of claim 1, comprising
   (a) introducing a nucleic acid molecule into cells, wherein the nucleic acid molecule encodes the fusion protein, and
   (b) expressing the fusion protein in the cells, whereby the fusion protein is produced.

9. A composition comprising the fusion protein of claim 1.

10. A virus like particle formed by the fusion protein of claim 1, wherein the target protein is displayed on the surface the virus like particle.

11. A composition comprising the virus like particles of claim 10.

12. A method of producing virus like particles, comprising
   (a) introducing a nucleic acid molecule into a cell, an organism or a portion of the organism, wherein the nucleic acid molecule encodes the fusion protein of claim 1,
   (b) expressing the fusion protein in the cell, the organism or the portion of the organism, and
   (c) forming virus like particles by the fusion protein, whereby the virus like particles are produced, wherein the target protein is displayed on the surface of the virus like particles.

13. A method of inducing an immunological response in a subject, comprising administering to the subject an effective amount of the fusion protein of claim 4 or virus like particles formed by the fusion protein of claim 4.

14. A method of treating a disease or condition in a subject, comprising administering to the subject an effective amount of the fusion protein of claim 5 or virus like particles formed by the fusion protein of claim 5.

15. A method of detecting a biomarker in a sample from a subject, comprising contacting the sample with an effective amount of the fusion protein of claim 6 or virus like particles formed by the fusion protein of claim 6, wherein the diagnostic agent binds the biomarker.

16. A method of catalyzing a reaction by a reagent, comprising contacting the reagent with an effective amount of the fusion protein of claim 7 or virus like particles formed by the fusion protein of claim 7, wherein the enzyme catalyzes the reaction.

* * * * *